United States Patent
Kohlmann et al.

(10) Patent No.: US 10,758,703 B2
(45) Date of Patent: Sep. 1, 2020

(54) SYSTEMS AND METHODS FOR PROVIDING A PULSE OF A THERAPEUTIC GAS WITH A DESIRED FLOW PROFILE TO MAXIMIZE THERAPEUTIC EFFECTIVENESS

(71) Applicant: INO Therapeutics LLC, Hampton, NJ (US)

(72) Inventors: Thomas Kohlmann, McFarland, WI (US); John Klaus, Cottage Grove, WI (US)

(73) Assignee: Mallinckrodt Hospital Products IP Limited, Dublin (IE)

( * ) Notice: Subject to any disclaimer, the term of this patent is extended or adjusted under 35 U.S.C. 154(b) by 1321 days.

(21) Appl. No.: 14/886,556

(22) Filed: Oct. 19, 2015

(65) Prior Publication Data

US 2016/0106949 A1 Apr. 21, 2016

Related U.S. Application Data

(60) Provisional application No. 62/065,046, filed on Oct. 17, 2014.

(51) Int. Cl.
*A61M 16/20* (2006.01)
*A61M 16/00* (2006.01)
(Continued)

(52) U.S. Cl.
CPC ...... *A61M 16/202* (2014.02); *A61M 16/0051* (2013.01); *A61M 16/024* (2017.08); *A61M 16/10* (2013.01); *A61M 16/12* (2013.01); *A61M 16/122* (2014.02); *A61M 16/20* (2013.01); *A61M 16/201* (2014.02);
(Continued)

(58) Field of Classification Search
CPC .. A61M 16/00; A61M 16/021; A61M 16/022; A61M 16/024; A61M 16/0051; A61M 16/0666; A61M 16/0672; A61M 16/10; A61M 16/1015; A61M 16/104; A61M 16/12; A61M 16/122; A61M 16/20; A61M 16/201; A61M 16/202;
(Continued)

(56) References Cited

U.S. PATENT DOCUMENTS

| 4,462,398 A | 7/1984 | Durkan et al. |
| 4,595,004 A | 6/1986 | Czech |

(Continued)

OTHER PUBLICATIONS

INOmax DS (Delivery System): Operation Manual (800 ppm INOMAX (nitric oxide) for Inhalation), *Ikaria, Inc.* 2010, 112 pages.

(Continued)

*Primary Examiner* — Colin W Stuart
(74) *Attorney, Agent, or Firm* — Servilla Whitney LLC

(57) ABSTRACT

Described are systems and methods for providing a pulse of a therapeutic gas with a desired flow profile to maximize therapeutic effectiveness. Systems and methods of the present disclosure can generate and/or provide desired flow profiles with various shapes and/or properties by configuring, modifying, optimizing, and/or factoring in aspects of at least one fixed flow rate assembly of a therapeutic gas delivery system such as, but not limited to, spatial relationships of elements of the fixed flow rate assembly, rate of valve closure and opening, latent flows, transient wave generation and/or propagation, to name a few.

19 Claims, 13 Drawing Sheets

(51) Int. Cl.
*A61M 16/10* (2006.01)
*A61M 16/12* (2006.01)

(52) U.S. Cl.
CPC ... *A61M 16/107* (2014.02); *A61M 2016/0021* (2013.01); *A61M 2016/0027* (2013.01); *A61M 2016/0039* (2013.01); *A61M 2205/502* (2013.01)

(58) Field of Classification Search
CPC .............. A61M 16/203; A61M 16/204; A61M 16/208; A61M 2016/102; A61M 2016/1035
USPC ....... 251/118, 123, 124, 119, 120, 121, 122, 251/125, 126, 127
See application file for complete search history.

(56) References Cited

U.S. PATENT DOCUMENTS

| | | | |
|---|---|---|---|
| 4,681,099 | A | 7/1987 | Sato et al. |
| 4,686,974 | A | 8/1987 | Sato et al. |
| 4,706,664 | A | 11/1987 | Snook et al. |
| 5,558,083 | A | 9/1996 | Bathe et al. |
| 5,732,693 | A | 3/1998 | Bathe et al. |
| 5,752,504 | A | 5/1998 | Bathe et al. |
| 6,125,846 | A | 10/2000 | Bathe et al. |
| 6,786,217 | B2 | 9/2004 | Stenzler |
| 7,523,752 | B2 | 4/2009 | Montgomery et al. |
| 8,282,966 | B2 | 10/2012 | Baldassarre et al. |
| 8,291,904 | B2 | 10/2012 | Bathe et al. |
| 8,293,284 | B2 | 10/2012 | Baldassarre et al. |
| 8,431,163 | B2 | 4/2013 | Baldassarre et al. |
| 8,573,209 | B2 | 11/2013 | Bathe et al. |
| 8,573,210 | B2 | 11/2013 | Bathe et al. |
| 8,770,199 | B2 | 7/2014 | Flanagan et al. |
| 8,776,794 | B2 | 7/2014 | Bathe et al. |
| 8,776,795 | B2 | 7/2014 | Bathe et al. |
| 8,795,741 | B2 | 8/2014 | Baldassarre |
| 8,846,112 | B2 | 9/2014 | Baldassarre |
| 9,086,313 | B2 | 7/2015 | Tobia et al. |
| 2004/0163647 | A1 | 8/2004 | Figley et al. |
| 2007/0089796 | A1* | 4/2007 | Electra Brown ....... B01F 3/026 137/896 |
| 2013/0098361 | A1 | 4/2013 | Kobrich et al. |

OTHER PUBLICATIONS

INOvent Delivery System: Operation and Maintenance Manual (CGA Variant), *Datex-Ohmeda, Inc.* 2000, 180 pages.
Using the INOpulse DS Subject Guide, *Ikaria, Inc.* 2012, 50 pages.
INOmax Label, Nitric Oxide Gas, *INO Therapeutics* 2013, 2 pages.
INOmax DSIR (Delivery System): Operation Manual (800 ppm INOMAX (nitric oxide) for Inhalation), Ikaria, Inc. 2012, 136 pages.

* cited by examiner

SYSTEMS AND METHODS FOR PROVIDING A PULSE OF A THERAPEUTIC GAS WITH A DESIRED FLOW PROFILE TO MAXIMIZE THERAPEUTIC EFFECTIVENESS

CROSS-REFERENCE TO RELATED APPLICATIONS

This application claims the benefit under 35 U.S.C. § 119(e) to U.S. Provisional Application No. 62/065,046, filed Oct. 17, 2014, the entire contents of which are incorporated herein by reference in their entirety

FIELD

The present disclosure generally relates to systems and methods for providing a pulse of a therapeutic gas with a desired flow profile to maximize therapeutic effectiveness.

BACKGROUND

A number of gases have been shown to have pharmaceutical action in humans and animals. One such gas is Nitric oxide (NO) that, when inhaled, acts to dilate blood vessels in the lungs, improving oxygenation of the blood and reducing pulmonary hypertension. Because of this, NO can be provided as a therapeutic pharmaceutical drug in gas form in the inspiratory breathing gases for patients with diseases (e.g., pulmonary hypertension).

The dosing of an inhaled pharmaceutical drug in gas form can be based on numerous variables. For example dosing can be based on the quantity of drug (usually in weight) per unit weight of the patient (e.g., mg/Kg) with the dose being specified to be delivered over a period of time or being repeated at specified intervals of time. This can allow users to control the quantity of drug and ensure the quantity of drug being delivered is in proportion to the patient's size. Further, this dosing technique can reduce the patient to patient variability in response to the drug due to the size of the patient (i.e. a 7 Kg baby will not get the same quantity of drug as a 80 Kg adult). Of course other techniques and/or variables can be used for dosing.

The dosing of a pharmaceutical drug in gas form for a pharmaceutical action and/or for a specific disease can have a tight window between the therapeutic level for the pharmaceutical drug and the level that causes harm. For example, various quantities of pharmaceutical gas can provide benefits to patients; however, if a pharmaceutical gas is delivered in too high a quantity then harm can be caused to a patient. For another example, timing delivery of pharmaceutical gas to various points during inspiration can provide benefits to patients; however, if delivery is timed to other points during inspiration the beneficial effects can be diminished and/or harm may be caused to a patient.

In light of at least these tight windows, it would be beneficial to deliver doses of a pharmaceutical drug in gas form to patients with specific flow profiles. However, these dosing flow profiles can be substantially complex and/or can require substantially accurate and precise quantities of gas that may be substantially small and/or that may vary with respect to substantially short durations of time. Further, generating and/or providing dosing with these specific flow profiles that have such requirements can be substantially difficult and require specific delivery systems that may require the use of expensive components. These expensive components can increase the cost of such systems, reduce availability to the public, and/or utilize resources that may be limited.

Accordingly, it would be advantageous to have a system and method that can accurately and precisely generate and/or provide pharmaceutical gases with specific desired dosing flow profiles. It would also be advantageous to have such as system and method be fabricated and/or utilize techniques that reduce costs, for example, to increase availability to the public and/or more effectively allow for use of resources.

SUMMARY

One aspect of the present invention relates to a system for providing a pulse of a pharmaceutical gas having a desired flow profile to deliver to a patient. In various embodiments of this aspect, the system comprises a first fixed flow rate assembly including a first fixed flow valve in fluid communication with a first fixed flow orifice, the first fixed flow valve being (1) a fixed flow valve that rapidly opens and rapidly closes, (2) located upstream or downstream of first fixed flow orifice and (3) at a volumetric offset from the first fixed flow orifice; and a flow delivery control that rapidly opens and rapidly closes the first fixed flow orifice located at least one of upstream or downstream of, and at the volumetric offset from, the first fixed flow valve to provide a pulse of a pharmaceutical gas having a desired flow profile to a patient.

In exemplary embodiments, the pulse of a pharmaceutical gas having a desired flow profile may provided to a patient to treat a specific disease, such as at least one of chronic obstructive pulmonary disease (COPD), idiopathic pulmonary fibrosis (IPF), and pulmonary hypertension (PH).

In exemplary embodiments, when the first fixed flow orifice is upstream to the first fixed flow valve at least one of (1) an initial flow spike in volume of transient therapeutic gas substantially equal to the volume in the volumetric offset is delivered when the first fixed flow valve is opened rapidly, and (2) a sharp cutoff is provided when the first fixed flow valve is closed rapidly.

In exemplary embodiments, when the first fixed flow orifice is downstream to the first fixed flow valve at least one of (1) a sharp turn on is provided when the first fixed flow valve is opened rapidly, and (2) a waning flow having a volume substantially equal to a volume in the volumetric offset is provided when the first fixed flow valve is closed rapidly.

In exemplary embodiments, when the first fixed flow orifice is upstream from the first fixed flow valve, the volumetric offset is substantially minimized to decrease duration of a waning flow generated when the first fixed flow valve is closed rapidly. In some embodiments, the volumetric offset has a volume of less than 1 mL. In some embodiments, the system of claim 6, wherein the volumetric offset has a volume in the range of 0.0005 mL to 0.1 mL.

In exemplary embodiments, the cannula or tube includes a dampener for ringing.

In exemplary embodiments, the desired flow profile for the pulse of pharmaceutical gas is one that minimizes the time that the first fixed flow valve is open. In some embodiments, the first fixed flow valve provides a pulse having a pulse width of less than 500 milliseconds.

Another aspect of the present invention relates to a method of providing a pulse of a pharmaceutical gas with a desired flow profile to deliver to a patient, the method comprising rapidly opening a first fixed flow valve that is located upstream from a first fixed flow orifice to commence delivery of a first dose of a pharmaceutical gas in a pulse having a desired flow profile to a patient that abruptly increases flow to a desired initial flow rate over negligible time; rapidly closing the first fixed flow valve to end flow, through the first fixed flow valve, of the pharmaceutical gas; and providing a waning flow of the pharmaceutical gas after rapidly closing the first fixed flow valve to complete delivery, to the patient, of the pulse of the pharmaceutical gas with the desired flow profile, wherein the waning flow is generated in response to arranging the first fixed flow valve at a volumetric offset from the first fixed flow orifice such that the waning flow is at least one of reduced by lessening the volumetric offset or increased by increasing the volumetric offset.

In exemplary embodiments, the pulse of a pharmaceutical gas having a desired flow profile is provided to a patient to treat at least one of chronic obstructive pulmonary disease (COPD), idiopathic pulmonary fibrosis (IPF), and pulmonary hypertension (PH).

In exemplary embodiments, the desired flow profile is downwardly sloped triangular shaped.

In exemplary embodiments, the method further comprises maintaining open the first fixed flow valve to continue delivery, to the patient, of the pulse of the pharmaceutical gas with the desired flow profile at a desired continued flow rate for a period of time. In some embodiments, the desired flow profile is quadrilateral shaped. In some embodiments, the volumetric offset has a volume of less than 1 mL and the quadrilateral is substantially rectangular shaped.

Another aspect of the present invention relates to a method of providing a pulse of a pharmaceutical gas with a desired flow profile to deliver to a patient, the method comprising rapidly opening a first fixed flow valve that is located downstream from a first fixed flow orifice to commence delivery of a first dose of a pharmaceutical gas in a pulse having a desired flow profile to a patient that abruptly increases flow to a desired initial flow rate including an initial flow spike over negligible time, wherein the initial flow spike is generated in response to arranging the first fixed flow valve at a volumetric offset from the first fixed flow orifice such that the initial flow spike is at least one of reduced by lessening the volumetric offset or increased by increasing the volumetric offset; rapidly closing the first fixed flow valve to end flow, through the first fixed flow valve, of the pharmaceutical gas to complete delivery, to the patient, of the pulse of the pharmaceutical gas with the desired flow profile.

In exemplary embodiments, the pulse of a pharmaceutical gas having a desired flow profile is provided to a patient to treat at least one of chronic obstructive pulmonary disease (COPD), idiopathic pulmonary fibrosis (IPF), and pulmonary hypertension (PH).

In exemplary embodiments, the method further comprises maintaining open the first fixed flow valve to continue delivery, to the patient, of the pulse of the pharmaceutical gas with the desired flow profile at a desired continued flow rate for a period of time.

In exemplary embodiments, the desired flow profile is quadrilateral shaped.

BRIEF DESCRIPTION OF THE DRAWINGS

The features and advantages of the present disclosure will be more fully understood with reference to the following, detailed description when taken in conjunction with the accompanying figures, wherein.

DETAILED DESCRIPTION

In exemplary embodiments, systems and methods of the disclosure provide pulse doses of a pharmaceutical gas with a desired flow profile to maximize therapeutic benefits, for example, for patients suffering from chronic obstructive pulmonary disease (COPD), idiopathic pulmonary fibrosis (IPF), and pulmonary hypertension (PH), cystic fibrosis (CF), to name a few. The desired flow profile can vary for substantially small doses of gas with respect to substantially short durations of time. Generating and/or providing these desired flow profiles with a substantially high degree of precision and accuracy can be difficult, but may be necessary to maximize therapeutic benefits. Noting this difficulty, systems and methods of the present disclosure can generate and/or provide desired flow profiles by configuring, modifying, optimizing, and/or factoring in aspects of at least one fixed flow rate assembly of a therapeutic gas delivery system.

Figure 1A:
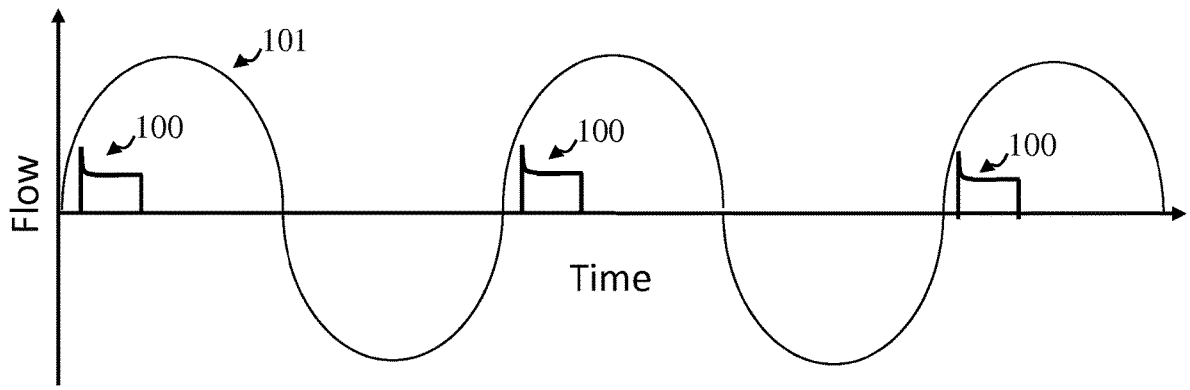
FIGS. 1A-1C illustratively depict exemplary desired flow profile for pulse doses of a pharmaceutical gas, in accordance with exemplary embodiments of the present disclosure.
Figure 1B:
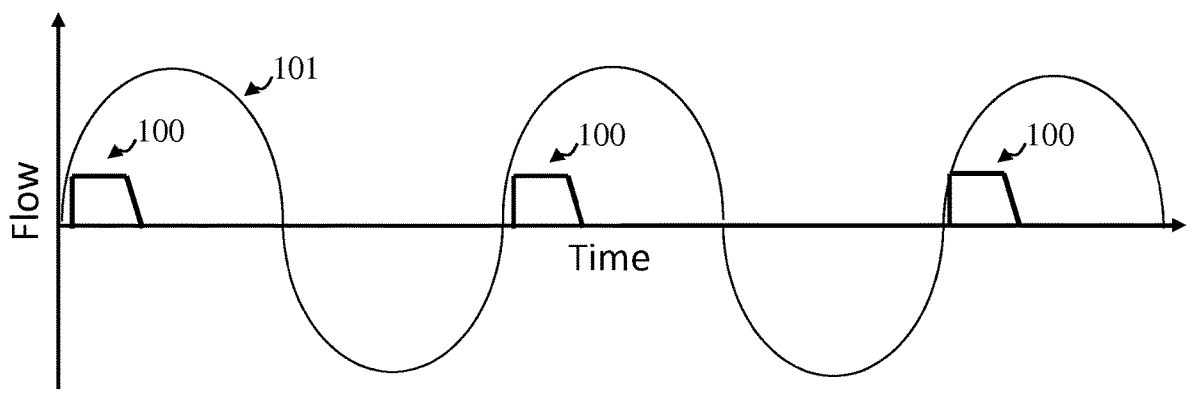
Figure 1C:
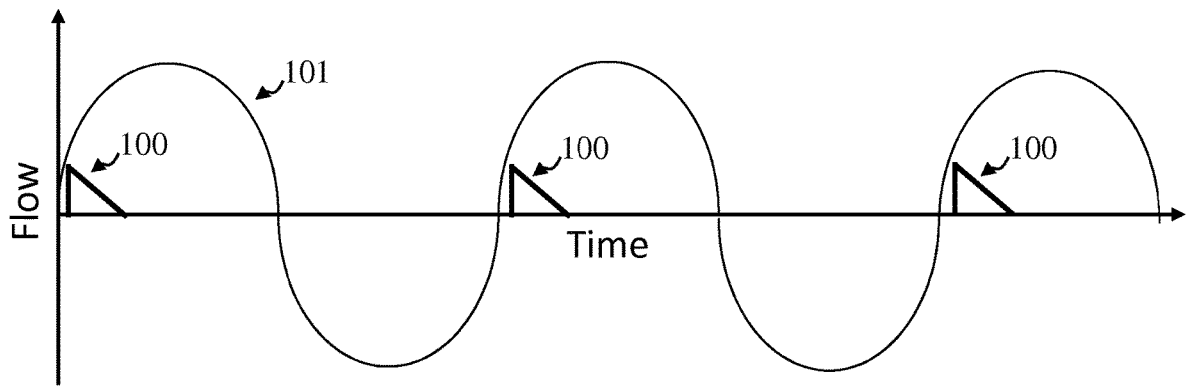

Referring to FIGS. 1A-1C, in exemplary embodiments, desired flow profile 100 for pulse doses of a pharmaceutical gas can vary for substantially small doses of gas with respect to substantially short durations of time can be delivered to a patient during specific points of the respiratory cycle 101. For example, desired flow profile 100 for pulse doses of a pharmaceutical gas can be delivered to a patient, during patient inspiration, during at least the first half of patient inspiration, during specific points of a patient's respiratory cycle, etc. Further, in exemplary embodiments, desired flow profiles can include shapes and/or properties (e.g., flow rate at a specific time, spikes in flow, waning tails, etc.).

In exemplary embodiments, shapes and/or properties of desired flow profiles for pulse doses of a pharmaceutical gas can be generated and/or provided for a specific pharmaceutical action and/or for a specific disease. For example, shapes and/or properties of desired flow profiles for pulse doses of a pharmaceutical gas can be can be generated and/or provided to provide benefits to patients suffering from COPD, IPF, CF, and PH, to name a few.

In exemplary embodiments, shapes and/or properties of desired flow profiles can be generated and/or provided by configuring, modifying, optimizing, and/or factoring in aspects of at least one fixed flow rate assembly of a therapeutic gas delivery system such as, but not limited to, spatial relationships of elements of the fixed flow rate assembly, rate of valve closure and opening, latent flows, transient wave generation and/or propagation, to name a few. By way of example, systems and methods of the present disclosure can generate and/or provide desired flow profiles by configuring, modifying, optimizing, and/or factoring in, amongst other things, (1) the rapid opening and closing the flow valve, (2) transient wave generation and/or propagation in response to the rapid opening and closing the flow valve, (3) the location of the flow valve upstream or downstream of the orifice, (4) the including and/or adjusting of a volumetric offset separating the flow valve from the orifice, and (5) the flow of a volume of gas affiliated with the volumetric offset, to name a few. Any of these variables and/or aspects can be configured, modified, optimized, and/or factored in to generate and/or provide desired flow profiles to patients suffering from COPD, IPF, CF, and PH, to name a few.

Further, in exemplary embodiments, systems and methods of the present disclosure can be used to modify and/or enhance previous systems and/or methods used to deliver pulse doses of a pharmaceutical gas so they can generate and/or provide these desired flow profiles without requiring substantially expensive components (e.g., expensive valve assemblies, etc.) and/or by utilizing newly discovered properties and/or techniques so the previous systems and/or methods can be enhanced, for example, without necessarily including substantially expensive components.

To provide and/or generate desired flow profiles, systems and methods of the present disclosure can use, modify, and/or be affiliated with various systems for delivering a pulse of a pharmaceutical gas to a patient. For example, systems and methods of the present disclosure can use, modify, and/or be affiliated with the teachings of U.S. Pat. No. 7,523,752 entitled "System and Method of Administering a Pharmaceutical Gas To A Patient", the content of which is incorporated herein by reference in its entirety and at least partially reproduced below. For ease, the systems and methods are disclosed, at times, as being used with, modifying, and/or being affiliated with the teachings of U.S. Pat. No. 7,523,752. This is merely for ease and is in no way meant to be a limitation.

In exemplary embodiments, providing and/or generating desired flow profiles for pulse doses of pharmaceutical gas, systems and methods of the present disclosure can determine, factor in, and/or allow setting of a desired quantity and/or duration of pharmaceutical gas therapy. For example, referring now to FIG. 2A, a front panel 10 of an apparatus is illustrated that can be modified and/or used in carrying out exemplary embodiments of the present disclosure. Front panel 10 can be a part of the apparatus and on that panel there can be input settings (e.g., input knobs) and displays which can allow the user to set and monitor the amount of pharmaceutical gas to be delivered to the patient.

The desired quantity of pharmaceutical gas to be delivered can be set and/or determined using a setting control including an input setting knob 12 and/or the set amount can be shown on the setting display 8. The units shown in FIG. 2A can be in milligrams per kilogram. The units can be measured in a dosage per kilogram of the patient's ideal body weight. Along with that input, there can be a further input 14 whereby the user can enter the patient's ideal body weight in kilograms and/or the amount can also displayed on the setting display 8. With those inputs, the user can set the quantity of the pharmaceutical gas to be administered to the patient in proportion to the size of the patient. This can be done to reduce the patient to patient variability in response to the pharmaceutical gas due to the size of the patient (i.e. a 7 kilogram baby will not be administered the same quantity of the pharmaceutical gas as a 80 kilogram adult).

Front panel 10 can also have a monitor display 6 which can display total dose of pharmaceutical gas (mg) to be delivered (e.g., shown at 16) as calculated for multiplying the dosage/kg by the patients ideal body weight in kg.

Once the desired quantity of gaseous drug has been set on the device the system can then determine the amount of pharmaceutical gas to be delivered in each breath and the amount of time and/or the number of breaths that it may take to deliver the total desired quantity of drug. Monitor display 6 can also display a running total of the delivered dose of pharmaceutical gas (mg) (e.g., shown at 17) as delivered to the patient so the user can monitor the progress of the treatment. This can be updated each breath as more pharmaceutical gas is delivered.

As stated, the units illustrated in FIG. 2A can be metric units, however, it will be understood that other units of mass and volume could be used in carrying out the present disclosure i.e. ounces and cubic inches and other designs of a front panel can be used as will later be understood.

Figure 2A:
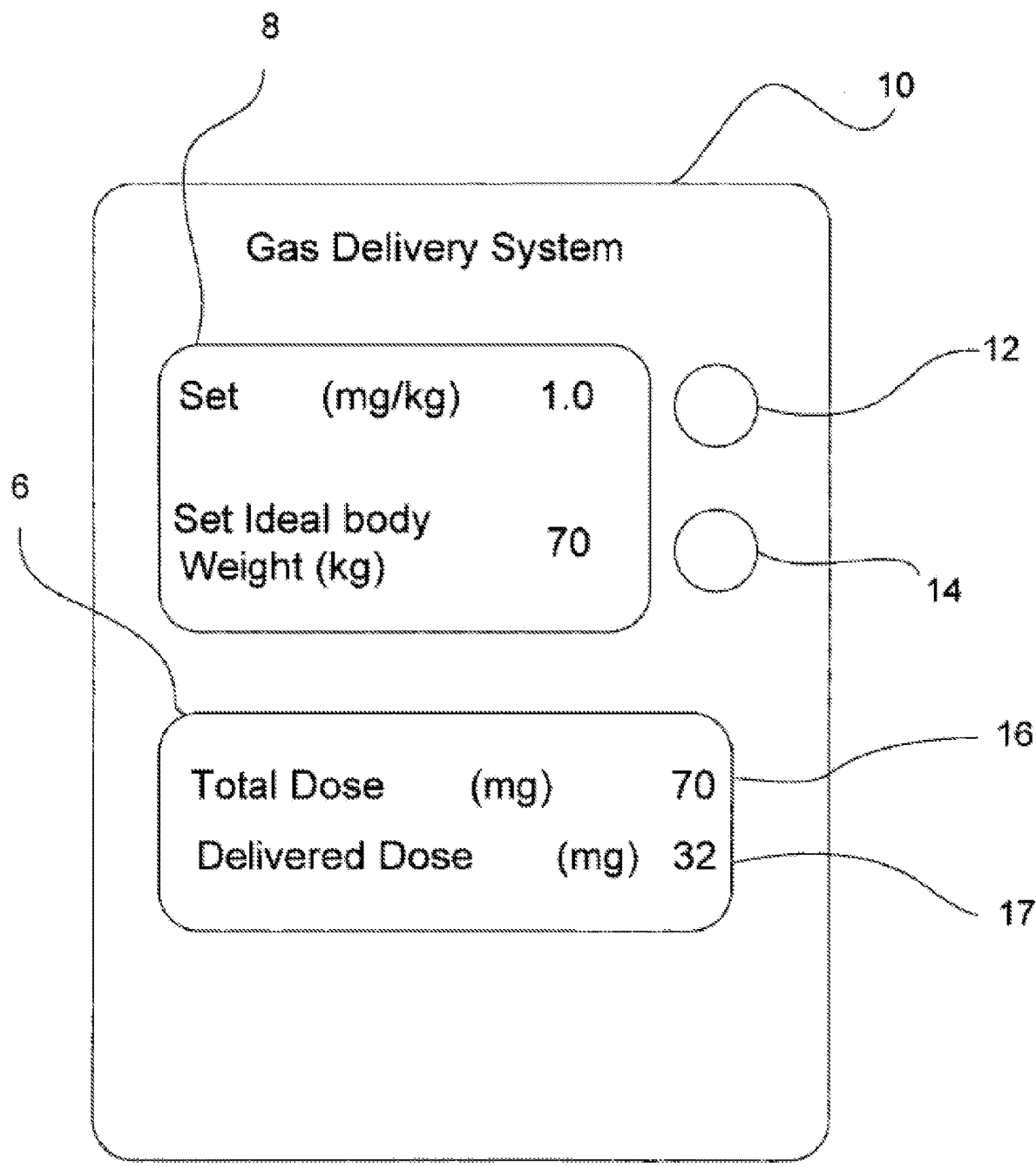
FIGS. 2A-2B illustratively depict an exemplary front panel of apparatuses that may be used for carrying out at least some aspects of the present disclosure, in accordance with exemplary embodiments of the present disclosure.
Figure 2B:
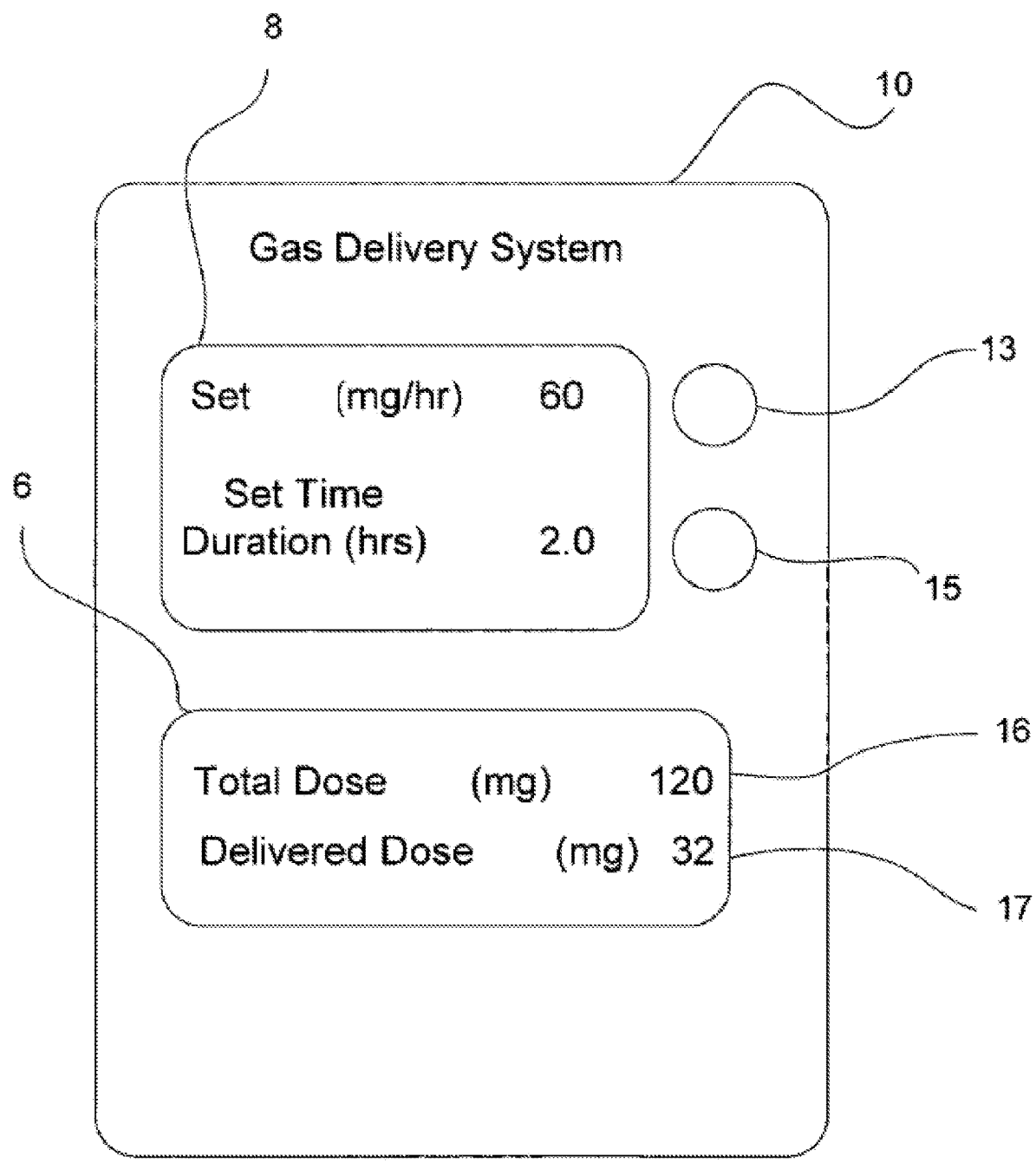

Referring to FIG. 2B, a similar front panel 10 for the apparatus as shown in FIG. 2A is depicted illustrating a different user setting option. The desired quantity of pharmaceutical gas to be delivered to the patient can be prescribed as a rate of delivery that can be set and/or determined using a setting control that can include an input setting knob 13 that can be in units of mass per time such as mg/hr of pharmaceutical gas to be delivered. In this option, the device can allow the time duration (e.g., in hours) of treatment to be set and/or determined, for example, using an input setting knob 15. If required, the input setting by input setting knob 15 could be set to continuous where the dose per hour would run continuously until the user changed the setting. With these input settings, the apparatus can calculate and/or display the desired quantity of the pharmaceutical gas to be administered to the patient.

Also, as in FIG. 2A, front panel 10 can also have a monitor display 6 which can display total dose of pharmaceutical gas (e.g., in mg) to be delivered (e.g., shown at 16) as calculated by multiplying the dosage/hr by the total time duration (e.g., hr.). Once the desired quantity of pharmaceutical gas has been set on the device, the system can then determine the amount of pharmaceutical gas to be delivered in each breath and the amount of time and/or the number of breaths that it will take to deliver the total desired quantity of drug. As before, monitor display 6 can display a running total of the delivered dose of pharmaceutical gas (mg) (e.g., shown at 17) as it is delivered to the patient so the user can monitor the progress of the treatment. This can be updated each breath as more pharmaceutical gas is delivered.

As can be appreciated, FIGS. 2A and 2B illustrate two of the many options for setting the desired quantity and duration of pharmaceutical gas therapy. These options are not meant to be exhaustive and there are other setting options described or that can be understood from the detailed descriptions that follow.

In exemplary embodiments, providing and/or generating desired flow profiles for pulse doses of pharmaceutical gas, systems and methods of the present disclosure can, determine, factor in, and/or allow setting of an amount of pharmaceutical gas to be delivered in each breath and an amount of time, and/or the number of breaths that it will take to deliver the desired quantity of pharmaceutical gas. For example, once the desired quantity of gaseous drug has been set and/or determined, the gas control system can then determine the amount of pharmaceutical gas to be delivered in each breath and the amount of time and/or the number of breaths that it will take to deliver the desired quantity of pharmaceutical gas.

There are a number of different approaches that the gas control system can use to determine the amount per breath and how long to deliver that dose so the desired quantity of pharmaceutical gas can be delivered independent of the respiratory pattern of the patient:

a) The user can set the quantity of pharmaceutical gas to be delivered during each breath ($M_{pg}$ breath) and the gas control system can calculate the number of breaths ($n_{breaths}$) which will be required to deliver the total quantity of pharmaceutical gas ($M_{pg}$) i.e.

$$n_{breaths} = M_{pg}/M_{pg\ breath} \quad (5)$$

Once the total number of breaths ($n_{breaths}$) required has been determined the value can be displayed on the front panel 12 by way of display 16 to inform the user of the number of breaths.

b) The user can set the number of breaths ($n_{breaths}$) that will administer the total quantity of the pharmaceutical gas and the system calculates the amount per breath ($M_{pg\ breath}$) to be delivered.

$$M_{pg\ breath} = M_{pg}/n_{breaths} (mg) \quad (6)$$

Once the amount per breath ($M_{pg\ breath}$) to be delivered has been determined, the value can be displayed on the front panel 10 to inform the user of the amount.

(c) The user could set the time duration for which the treatment is to be delivered over. The amount per breath may then be determined by calculating the quantity per minute and then, for example, by monitoring the patient's respiration rate in breaths per minute, the amount per breath can be calculated. This calculation can be repeated after every breath so any changes in the patients respiratory rate does not affect the overall quantity of gaseous drug being delivered.

d) If the desired quantity of pharmaceutical gas was entered as a dose per Kg of the patient's ideal body weight (μg/kg) along with the patient's ideal body weight (Kg) then the amount per breath ($M_{pg\ breath}$) can be determined as a function of the patient's ideal body weight (IBW), the set dose per kilogram ($M_{kg}$) and the patient's monitored respiratory rate (RR) or combinations thereof;

$M_{pg}$ breath=f(IBW, $M_{kg}$, RR) and the number of breaths can then be calculated as;

$$n_{breaths} = M_{pg}/M_{pg\ breath} \quad (7)$$

Once the amount per breath ($M_{pg\ breath}$) and the number of breaths ($n_{breaths}$) required to be delivered has been determined, the values can be displayed on the front panel 10 to inform the user of the amounts the device has selected.

e) Instead of the ideal body weight (IBW) of the patient, the height and sex of the patient could be entered (which is how IBW is determined).

f) If the desired quantity of pharmaceutical gas per unit of time is entered into the device, then the device can calculate the quantity per breath to be delivered to the patient based on the current monitored respiratory breath rate (as determined by the breath trigger sensor). This quantity per breath can be recalculated after every breath when new information on the respiratory rate is available to ensure the quantity per unit of time is maintained even if the patient respiratory breath pattern changes over time.

g) There can also be other ways of varying the quantity of pharmaceutical gas delivered per breath to ensure the quantity per unit of time is maintained even if the patients respiratory rate changes. Another example may be where the device has two different amounts of delivery per breath, a high amount and a low amount. The device chooses which one to use based on the calculated quantity per unit of time being delivered over the past number of breaths. If the amount per unit of time is greater than required, it uses the low amount per breath until the situation corrects itself; likewise, if the quantity per unit of time is running low, then the unit switches to the high amount per breath.

The device can also have programmed limits which restrict the maximum and minimum values that can be selected for $M_{pg}$ breath so that the system doesn't select inappropriately too high or too low values. These limits can be set to vary based on the patient's ideal body weight, or other indicator of the patient size such as the patient's height, or the respiratory rate of the patient.

The aforesaid information can be utilized to deliver the dose to the patient and to determine the amount per breath, time of administration, and/or other parameter in order to commence the administration of pharmaceutical gas and/or to terminate that administration when the user set quantity of the pharmaceutical gas has been delivered to the patient. Further, in exemplary embodiments, doses delivered to the patient can be provided and/or generated in pulses of pharmaceutical gas that can include desired flow profiles.

Figure 3:
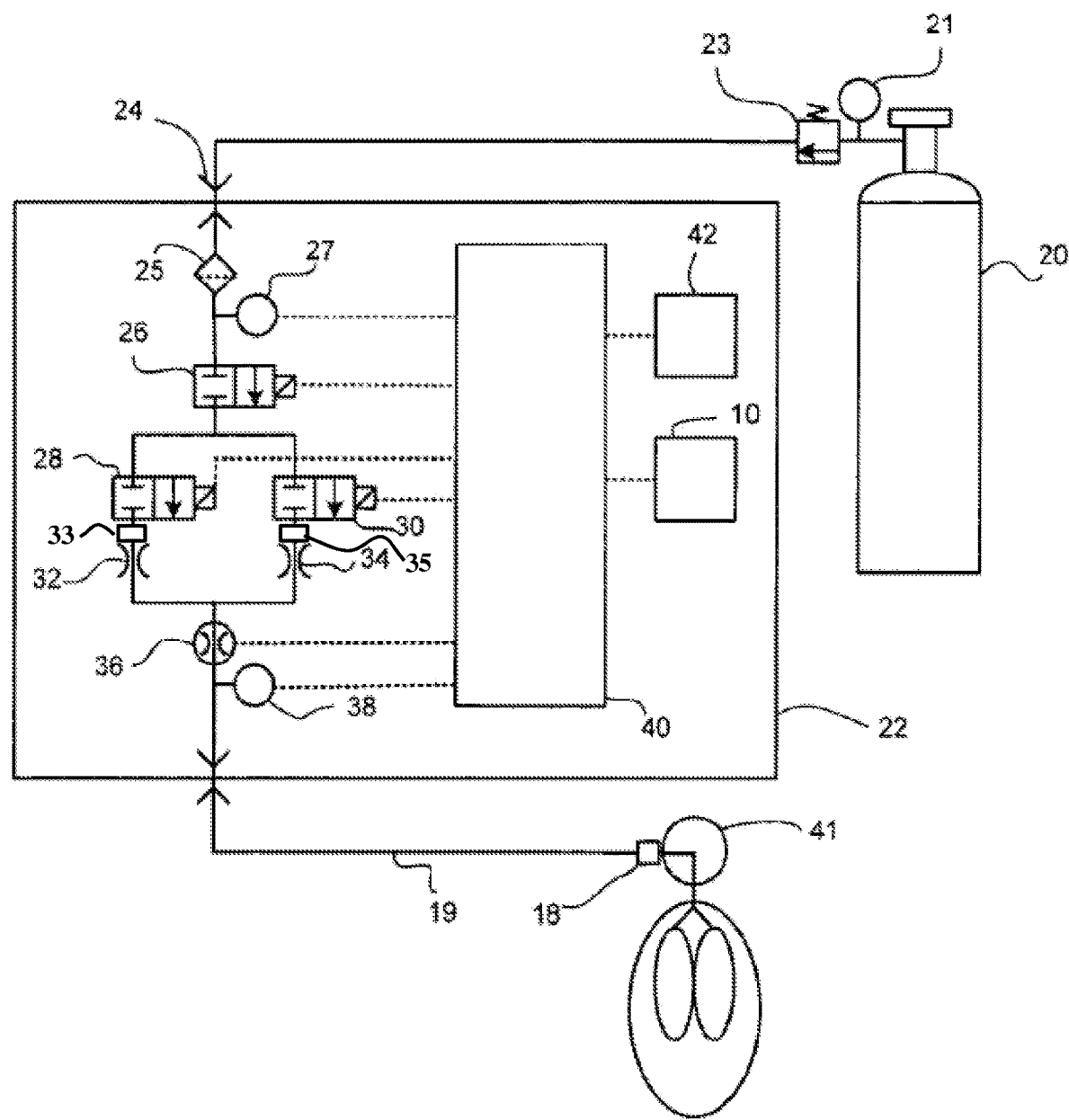
FIG. 3 is an exemplary schematic view of apparatuses that can be used and/or modified to carry out at least some aspects of the present disclosure, for example, with a spontaneously breathing patient, in accordance with exemplary embodiments of the present disclosure.

Turning now to FIG. 3, there is shown a schematic of a system comprising various elements that can be used and/or modified to carry out various exemplary embodiments of the present disclosure, for example, when the patient is breathing spontaneously and/or that can be used and/or modified to provide and/or generate desired flow profiles for pulse doses of pharmaceutical gas, for example, when the patient is breathing spontaneously. As can be seen, a patient device 18 can deliver the dosage of the pharmaceutical gas from a gas delivery system 22 to a patient 41 via a gas conducting conduit 19. As indicated, patient device 18 can be any one of a variety of devices that may actually direct the pharmaceutical gas into the patient and/or may be a nasal cannula, a mask, an endotracheal tube and the like, to name a few.

In exemplary embodiments, there can be a source of the pharmaceutical gas that can be a gas supply tank 20 containing the pharmaceutical gas generally in a carrier gas. When the pharmaceutical gas is carbon monoxide, for example, the conventional, commercially available carrier gas may be air. The supply of carbon monoxide and air can be provided in concentrations of 3000 ppm however, concentrations within the range of 1000 to 5000 ppm of pharmaceutical gas in air may also be possible alternatives. In the case of NO as the pharmaceutical gas, the carrier gas may be nitrogen and that may be available in concentrations range from 100 ppm to 5000 ppm. Of course other concentrations can be used and/or provided.

Accordingly, from supply tank 20, there can be a tank pressure gauge 21 and a regulator 23 to bring the tank pressure down to the working pressure of gas delivery system 22. The pharmaceutical gas can enter gas delivery system 22 through an inlet 24 that can provide a ready connection between delivery system 22 and supply tank 20 via a conduit. Gas delivery system 22 can have a filter 25 to ensure no contaminants can interfere with the safe operation of the system and/or a pressure sensor 27 to detect if the supply pressure is adequate and can thereafter include a gas shut off valve 26 as a control of the pharmaceutical gas entering deliver system 22 and to provide safety control in the event delivery system 22 is over delivering the pharmaceutical gas to the patient. In the event of such over delivery, shut off valve 26 can be immediately closed and an alarm 42 can be sounded to alert the user that the gas delivery system has been disabled. As such, shut off valve 26 can be a solenoid operated valve that can be operated from signals directed from a central processing unit including a microprocessor.

Downstream from shut off valve 26 can be a flow control system that controls the flow of the pharmaceutical gas to the patient through patient device 18. In exemplary embodiments, the flow control system can comprise a first flow control valve that can be a high flow control valve 28 and a second flow control valve that can be a low control valve 30 and just downstream and/or upstream (not shown) from flow control valves 28, 30, respectively, there can be a first flow orifice that can be a high flow orifice 32 and a second flow orifice that can be a low flow orifice 34. The purpose and use of the flow valves 28, 30 and flow orifices 32, 34 will be later explained. A gas flow sensor 36 can also be located in the flow of pharmaceutical gas to patient device 18 and, as shown, can be downstream from the flow control system, however, gas flow sensor 36 may alternatively be located upstream of the flow control system.

In exemplary embodiments, volumetric offset (e.g., volumetric offset 33 and 35) can be located between and/or can separate flow valves (e.g., flow valves 28 and 30) from orifices (e.g., flow orifices 32 and 34) such that a volume of gas can be in the volumetric offset. The purpose and use of volumetric offset 33 and 35 as well as flow valves 28, 30 and flow orifices 32, 34 will be later explained.

Next, there can be a patient trigger sensor 38. When the patient breathes in during inspiration it can create a small sub atmospheric pressure in the nose or other area where patient device 18 is located, and hence in patient device 18 itself. Patient trigger sensor 38 can detect this pressure drop and can provide a signal indicative of the start of inspiration of the patient. Similarly, when the patient breathes out there can be a positive pressure in patient device 18 and patient trigger sensor 38 can detect that positive pressure and can provide a signal indicative of the beginning of expiration. This can allow patient trigger sensor 38 to determine not only the respiratory rate of the patient but also the inspiratory times and/or expiratory times. It will be understood that other techniques can be used to determine the respiratory rate of the patient, inspiratory times, and expiratory times, and/or other aspects of patient breathing.

Finally there can be a central processing unit (CPU) 40 that can communicate with patient trigger sensor 38, flow valves 28, 30, gas shut off valve 26, and other components in order to carry out various exemplary embodiments of the present disclosure. CPU 40 can include a processing component such as a microprocessor to carry out all of the solutions to the equations that can be used by the gas delivery system 22 to deliver the predetermined quantity of the pharmaceutical gas to a patient. The CPU 40 can be connected to the front panel 10 where the user can enter settings and monitor therapy.

In exemplary embodiments, various elements of delivery system 22 can be used and/or modified to carry out various exemplary embodiments of the present disclosure when spontaneous breathing occurs. Also, in exemplary embodiments, various elements of delivery system 22 can be used and/or modified to provide and/or generate desired flow profiles for pulses of pharmaceutical gas. By way of example, when delivery system 22 detects, (e.g., by way of patient trigger sensor 38) that inspiration has started, a signal can be provided to CPU 40 to deliver a dose of a pharmaceutical gas ($M_{pg}$ breath) into the patient's inspiratory gas flow, preferably during the first ½ of the inspiratory cycle. This amount per breath can have been determined based on the desired quantity of pharmaceutical gas that may have been set on the system and the calculations made in a) to g) described earlier.

The actual volume of gas delivered during the breath can depend on the concentration of the pharmaceutical gas in the carrier gas supplied by supply tank 20. A typical source concentration ($C_{pg}$) for pharmaceutical gas can be 3000 ppm (range 500 to 5000). The volume of source gas ($V_d$) per breath to provide a dose per breath ($M_{pg}$ breath) when the source of pharmaceutical gas is 3000 ppm can be given by the following equation, combining equations 2, 3, 4 and 6;

$$V_d = M_{pg\ breath} / (28 \cdot C_{pg} \cdot 4.16 \times 10^{-11}) \quad (8)$$

Given that $M_{pg} = 60 \times 10^{-3}$ (g), $C_{pg} = 3000$ (ppm), $n_{breaths} = 600$, then $V_d = 28.6$ (mL).

To deliver the volume of source gas per breath ($V_d$), that is, the pharmaceutical gas and the carrier gas, delivery system 22 can open a flow control valve, such as a first flow valve that can be high flow valve 28 and/or a second flow valve that can be a low flow valve 30 to allow the gas to flow to the patient until the volume per breath ($V_d$) has been delivered. The presence of the first flow orifice that can be high flow orifice 32 and the second flow orifice that can be low flow orifice 36 can limit the flow of gas to a fixed set level during the period that flow valves 28, 30 are open so delivery system 22 can determine the period of time flow valves 28, 30 should be open to deliver the volume per breath ($V_d$) required. Also, the flow can be determined by gas flow sensor 36 to monitor the gas flow to patient device 18 and thus to the patient and can shut off the appropriate flow control valve 28, 30 when the desired predetermined quantity of pharmaceutical gas dose has been delivered to the patient.

In exemplary embodiments, to provide enough range to cover all the possible doses, the use of multiple flow valves such as, but not limited to, flow valve 28 and flow valve 30 along with corresponding multiple orifices, flow orifice 32 and flow orifice 34, can be used in parallel so as to provide ranges of gas flow. For instance, gas flow through flow valve 30 could be set to 1 L/min and gas flow through flow control valve 28 could be set to 6 L/min. The flow range of the particular gas flow valve can be selected to ensure that the volume of gas per breath ($V_d$) can be delivered to the patient in at least ½ the inspiratory time.

As an example, if the patient was breathing at 12 breaths per minute and had an I:E ratio of 1:2 then the inspiratory time would be 1.66 seconds and half that would be 0.83 seconds.

The time (t) taken to deliver a $V_d$ of 28 mL can be calculated as follows.

$$t=V_d 60/(Q \cdot 1000) \text{ (secs)} \quad (9)$$

When Q (the flow of gas when the flow valve 28 is open)=6 L/mins t=0.28 (secs).

That time is therefore well within ½ the inspiratory time allowed of 0.83 seconds.

Delivery system 22 can also include monitoring and alarm features to alert the user if delivery system 22 is, for example, not working correctly. Those alarm conditions can be determined by CPU 40 and/or alarm 42 can be activated to alert the user to the particular fault condition. Alarm 42 can be audible, visual or both and the alarm conditions can be any one or all of the following: No breath detected Low source gas pressure Inaccurate delivery of the volume per breath ($V_d$), Over delivery of the volume per breath ($V_d$), Under delivery of the volume per breath ($V_d$), to name a few.

Under certain conditions, such as when the delivery system 22 is over delivering the pharmaceutical gas, CPU 40 may signal gas shut off valve 26 and immediately cease any further delivery of the pharmaceutical gas and/or alarm 42 may also be activated.

The use of alarm 42 can also be an alternative to actually shutting off the supply of the pharmaceutical gas to a patient when the predetermined desired quantity of pharmaceutical gas has been fully delivered to the patient. In such case, as an alternative to ceasing the further supply of the pharmaceutical gas to the patient, delivery system 22 may, by way of CPU 40, activate alarm 42 to alert the user that the total predetermined desired quantity of the pharmaceutical gas has been delivered. The user can then determine whether to manually deactivate delivery system 22 or continue the delivery of the pharmaceutical gas, for example, under more watchful control of the patient's status.

Figure 4:
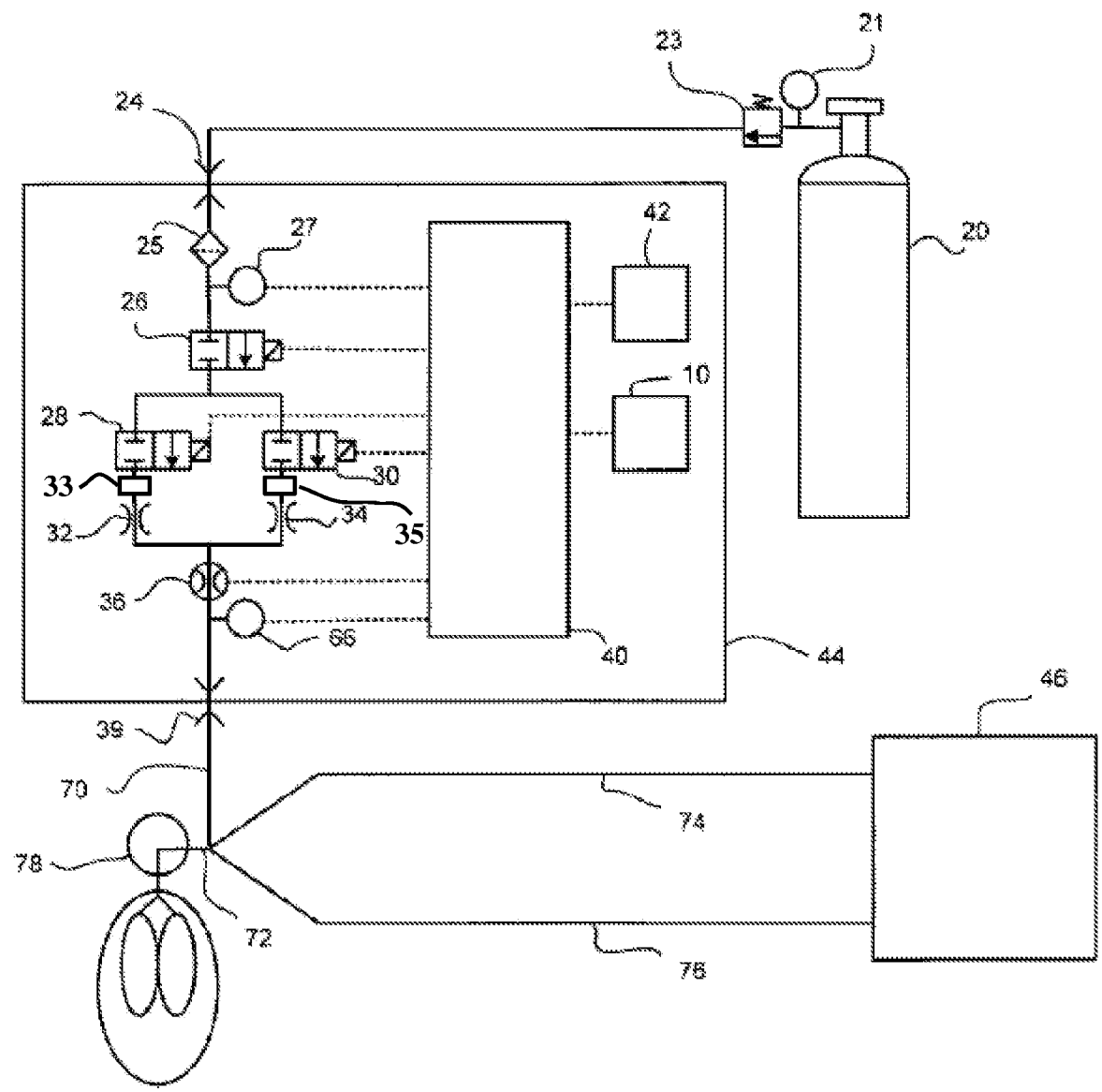
FIG. 4 is an exemplary schematic view of apparatuses that can be used and/or modified to carry out at least some aspects of the present disclosure, for example, with a patient being breathed by way of a ventilator, in accordance with exemplary embodiments of the present disclosure.

Turning now to FIG. 4, there is shown a schematic view of a gas delivery system 44 used in conjunction with a patient being breathed by a ventilator 46. Various elements of gas delivery system 44, used in conjunction with ventilator 46, can used and/or modified to provide and/or generate desired flow profiles for pulses of pharmaceutical gas. Similar to FIG. 3, again there is a supply tank 20 that can include a conventional gas regulator 23 and a pressure gauge 21 to supply the pharmaceutical gas along with the carrier gas to an inlet 24 in gas delivery system 44. Briefly summarizing the components of the FIG. 4, since they may be basically the same components as described with respect to the FIG. 3, there can be a filter 25 and a pressure sensor 27 in gas delivery system 44. Again there can be a shut off valve 26 to control the overall flow of the pharmaceutical gas through gas delivery system 44.

Flow control valves 28 and 30 can control the flow of the pharmaceutical gas through gas delivery system 44 and, flow valves 28, 30 can operate as described with respect to the FIG. 3 with flow orifices 32, 34 located downstream and/or upstream (not shown) of the flow control valves.

Further, volumetric offset 33 and 35 can be located between and/or can separate flow valves 28 and 30 flow orifices 32 and 34 such that a volume of gas can be in the volumetric offset.

Again there can be a gas flow sensor 36 and/or a patient trigger sensor 66, both of which can communicate with a CPU 40. In exemplary embodiments, the pharmaceutical gas can be carried through an outlet conduit 70 to a patient device 72 that can also receive breathing gas from ventilator 46. As such, ventilator 46 can deliver a flow of gas through an inspiratory limb 74 and gas can be returned to ventilator 46 through an expiratory limb 76.

The flow of gas from ventilator 46 can thus be supplemented by the flow of pharmaceutical gas from gas delivery system 44 where that gas may be mixed at, or proximate to, patient device 72 for introduction into patient 78. Since the pharmaceutical gas can be delivered to the patient over the plurality of breaths, as disclosed above, CPU 40 can carry out the same and/or similar determinations of flows and the like as explained with respect to the FIG. 3. A difference between FIG. 4 and that shown in FIG. 3 is that the patient trigger sensor 66 can be designed to operate in a way that works with ventilator 46.

For instance, when ventilator 46 provides gas flow to a patient during inspiration, it can cause a positive pressure in the breathing circuit. The positive pressure can be conducted through outlet conduit 70 and can be detected by patient trigger sensor 66 and can be recognized as the start of inspiration. This is unlike exemplary embodiments of FIG. 3 where the patient breathes spontaneously and a negative pressure can be generated during inspiration in patient device 18; this negative pressure can be conducted to patient trigger sensor 38 of FIG. 3 and can be recognized as the start of inspiration. As can be appreciated, patient trigger sensor 38 of FIG. 3 and patient trigger sensor of FIG. 4 could be the same pressure sensor and gas delivery system 44 can be set for work with a ventilator or a spontaneously breathing patient.

In exemplary embodiments, the shape and/or properties of desired flow profiles generated and/or provided by a pharmaceutical gas delivery system can be based on aspects such as, but not limited to, spatial relationships of elements of the fixed flow rate assembly, rate of valve closure and opening, latent flows, and/or transient wave generation and/or propagation. By way of example, systems and methods of the present disclosure can generate and/or provide desired flow profiles by configuring, modifying, optimizing, and/or factoring in, amongst other things, (1) the rapid opening and closing the flow valve, (2) transient wave generation and/or propagation in response to the rapid opening and closing the flow valve, (3) the location of the flow valve upstream or downstream of the orifice, (4) the including of a volumetric offset separating the flow valve from the orifice, and (5) the flow of a volume of gas affiliated with the volumetric offset.

Using systems and methods of the present disclosure variables and/or aspects can be configured, modified, optimized, and/or factored in to generate and/or provide desired flow profiles to patients suffering from COPD, IPF, and PAH, to name a few. At times, the name of a specific disease may not be provided; however, this is merely for ease.

Figure 5A:
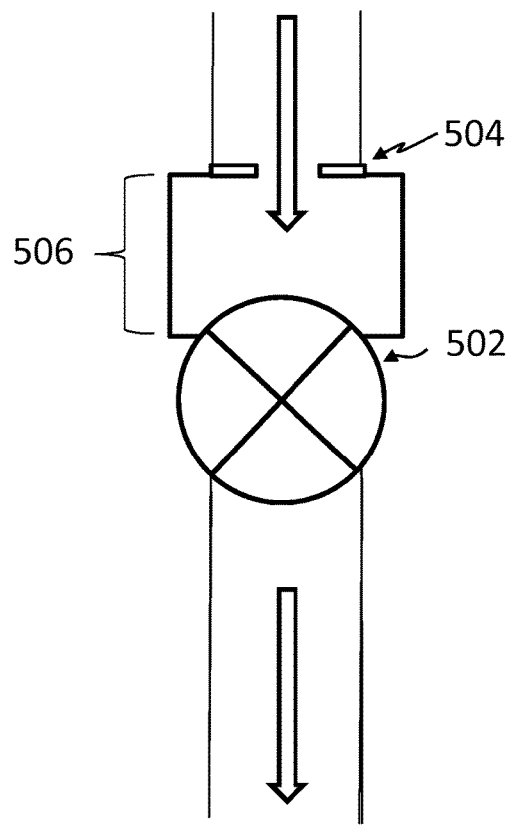
FIGS. 5A-5D illustratively depict configurations for generating exemplary desired flow profile, in accordance with exemplary embodiments of the present disclosure.
Figure 5C:
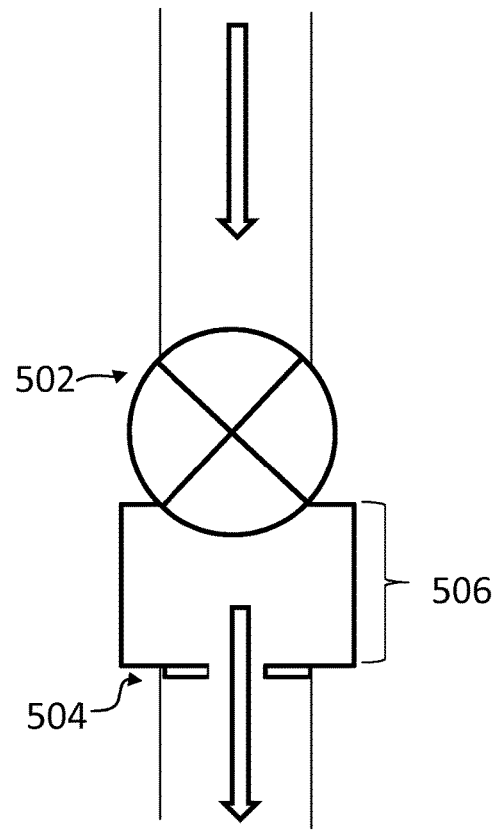
Figure 5B:
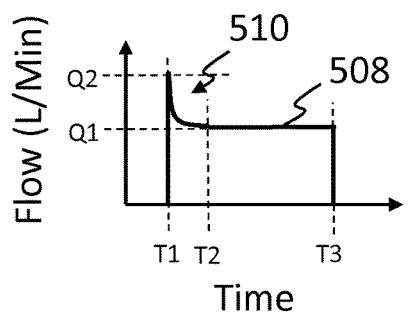
Figure 5D:
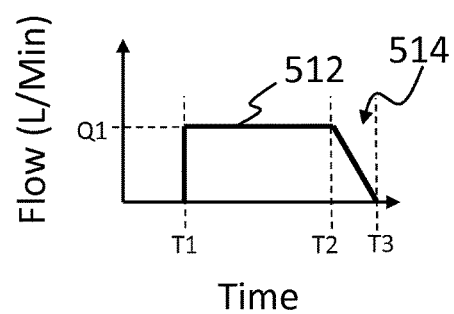
Figure 6A:
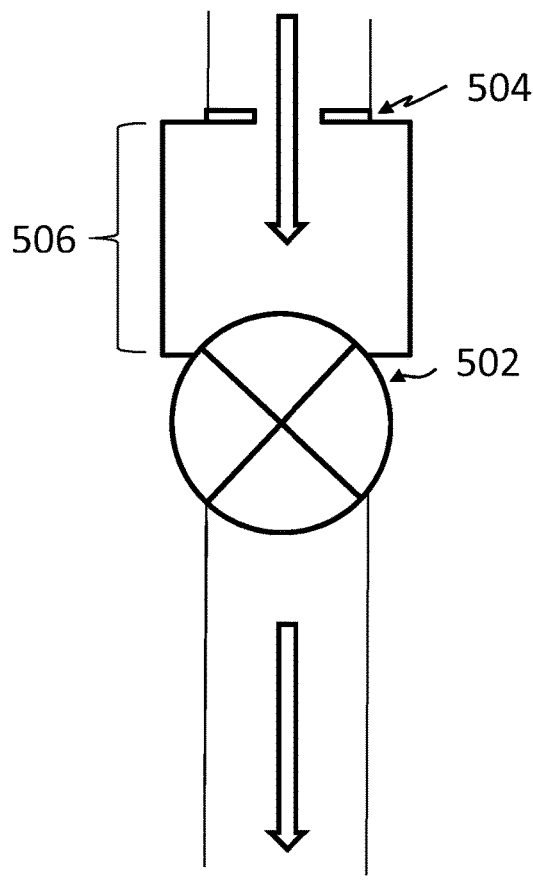
FIGS. 6A-6D illustratively depict modifying at least exemplary volumetric offsets and/or generating initial flow spikes, in accordance with exemplary embodiments of the present disclosure.
Figure 6C:
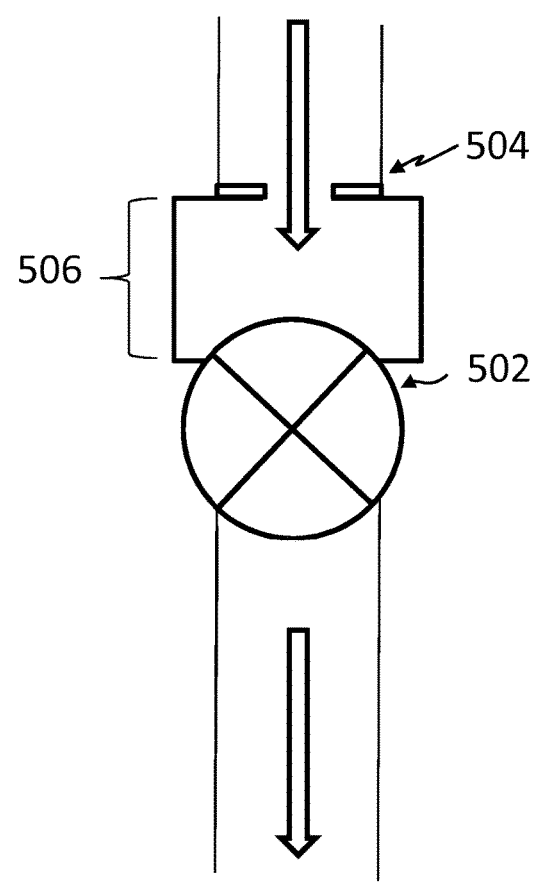
Figure 6B:
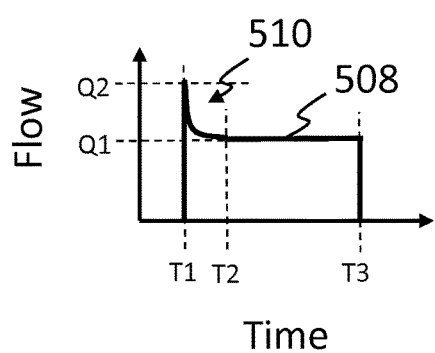
Figure 6D:
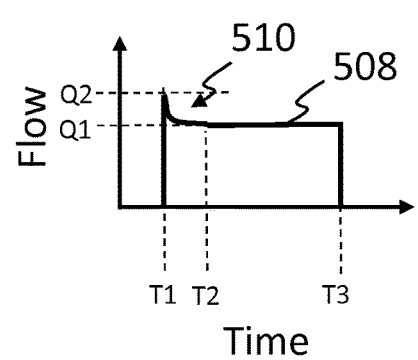
Figure 7A:
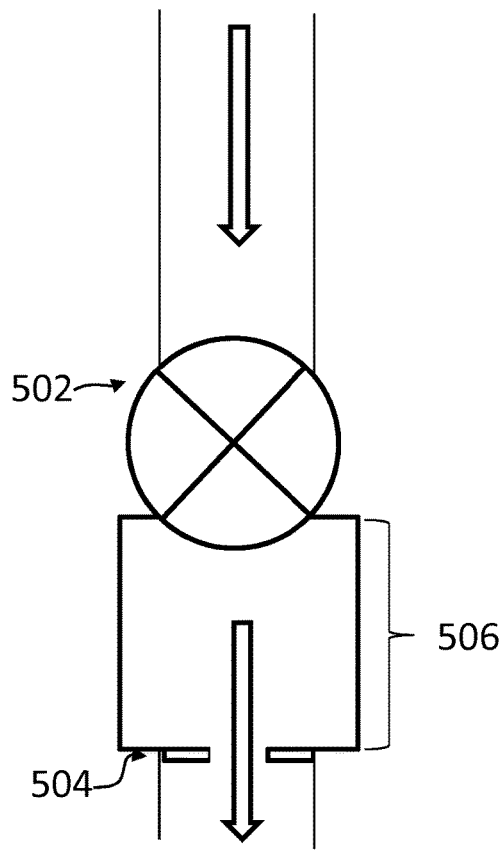
FIGS. 7A-7D illustratively depict modifying at least exemplary volumetric offsets and/or generating waning flows, in accordance with exemplary embodiments of the present disclosure.
Figure 7C:
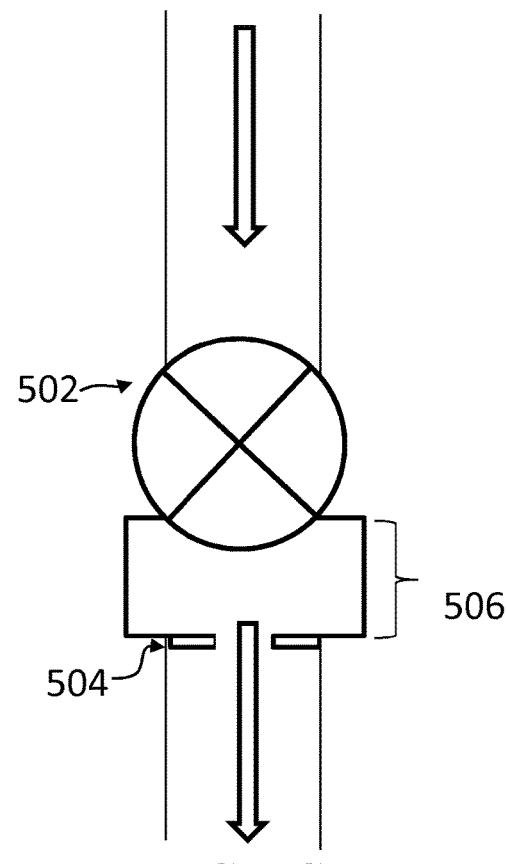
Figure 7B:
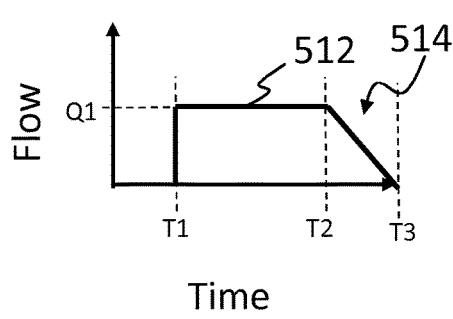
Figure 7D:
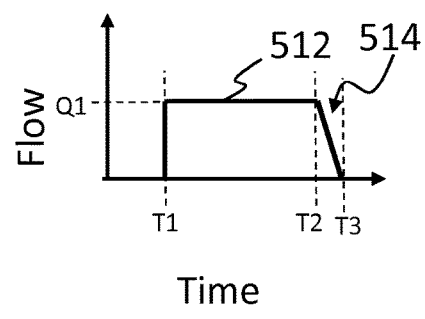
Figure 8A:
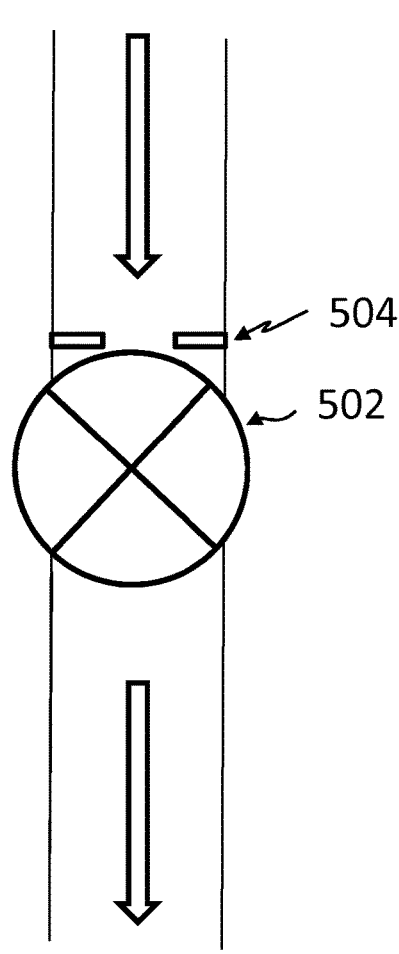
FIGS. 8A-8D illustratively depict modifying at least exemplary volumetric offsets and/or generating pulse waves, in accordance with exemplary embodiments of the present disclosure.
Figure 8C:
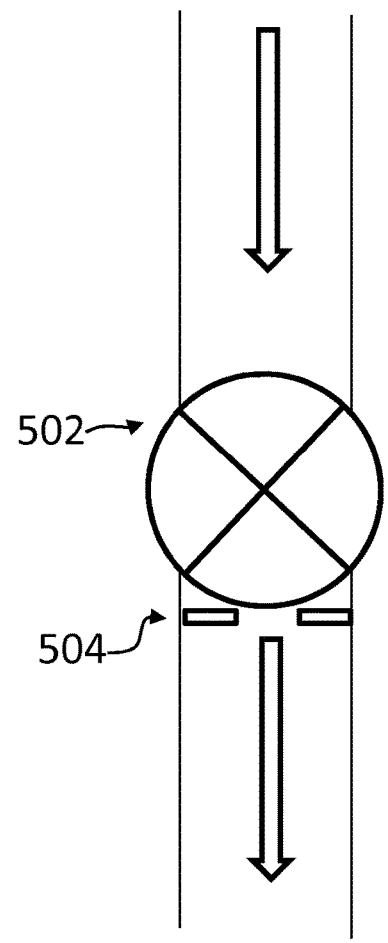
Figure 8B:
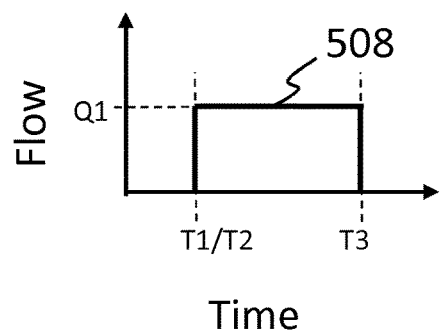
Figure 8D:
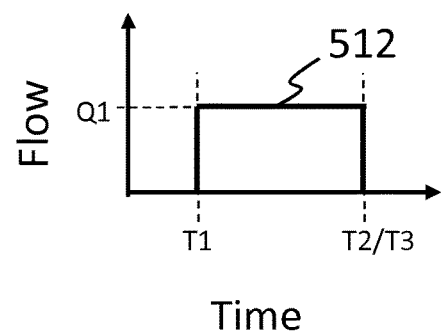
Figure 9A:
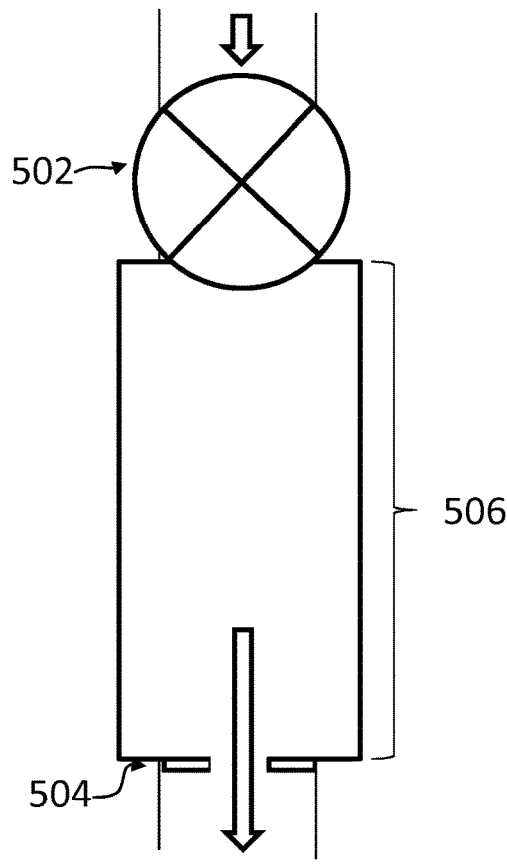
FIGS. 9A-9D illustratively depict modifying at least exemplary volumetric offsets and/or generating waning flows, in accordance with exemplary embodiments of the present disclosure.
Figure 9C:
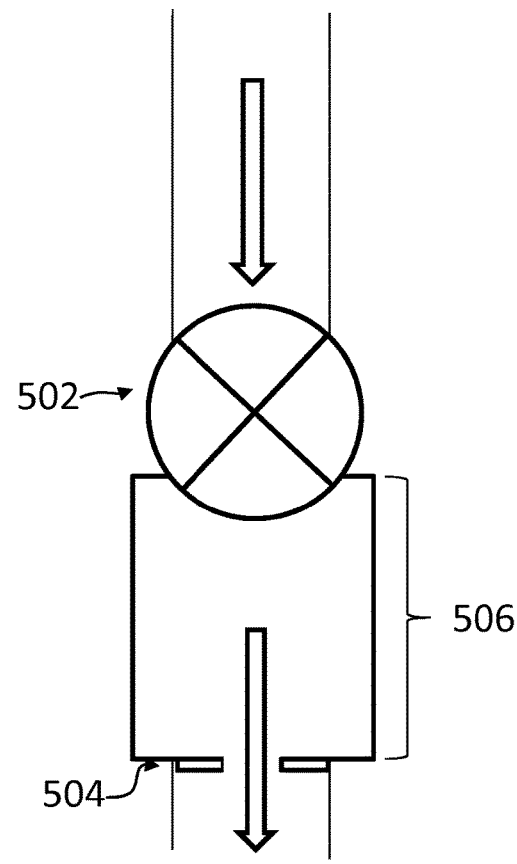
Figure 9B:
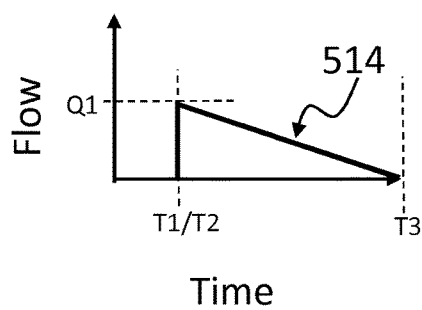
Figure 9D:
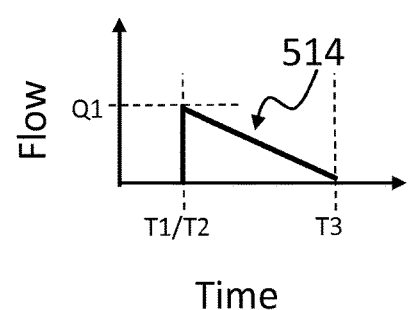
Figure 10A:
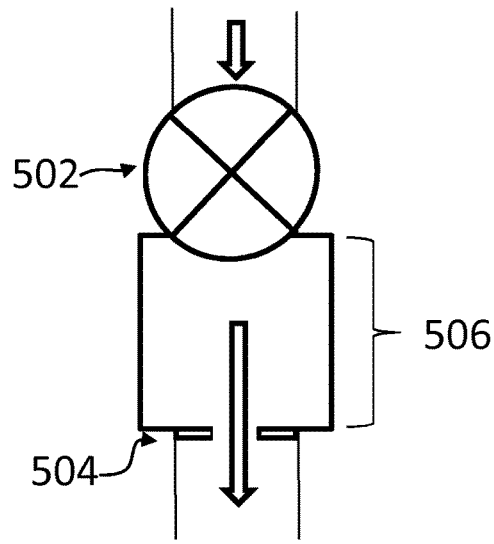
FIGS. 10A-10H illustratively depict exemplary volumetric offsets, in accordance with exemplary embodiments of the present disclosure.
Figure 10B:
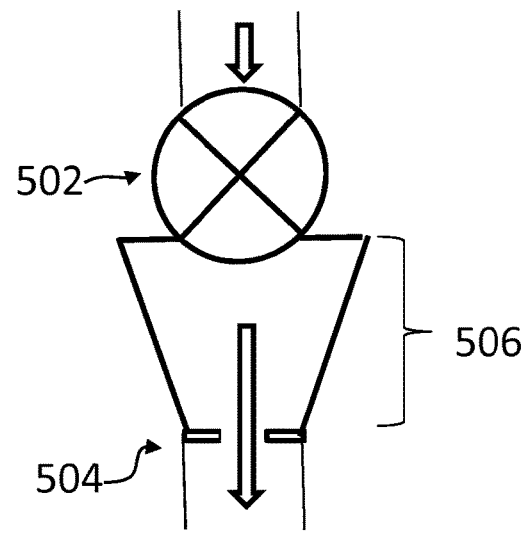
Figure 10C:
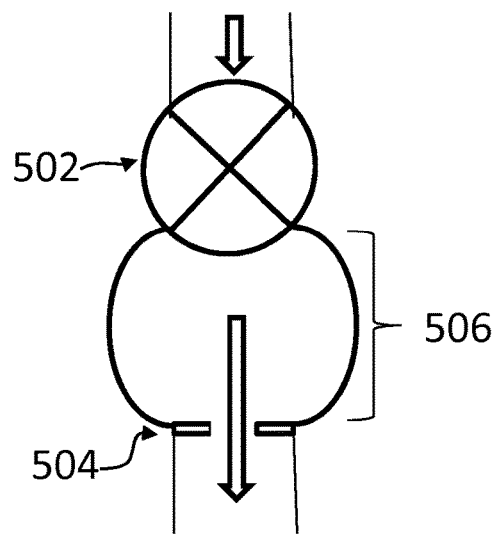
Figure 10D:
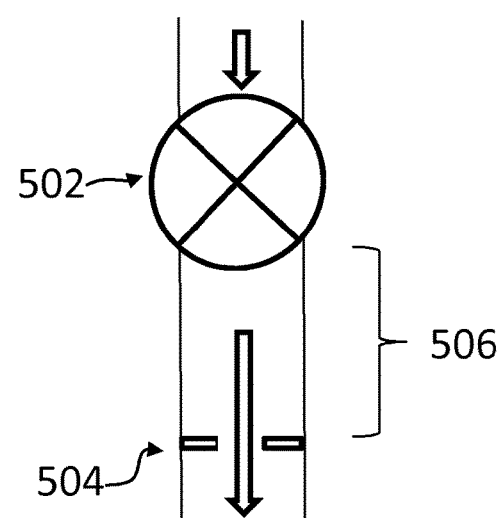
Figure 10E:
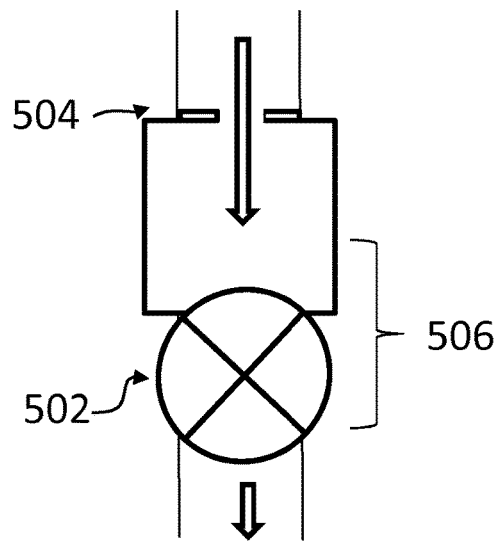
Figure 10F:
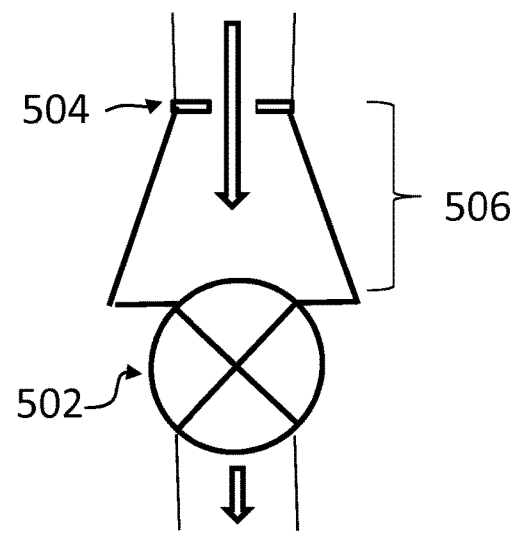
Figure 10G:
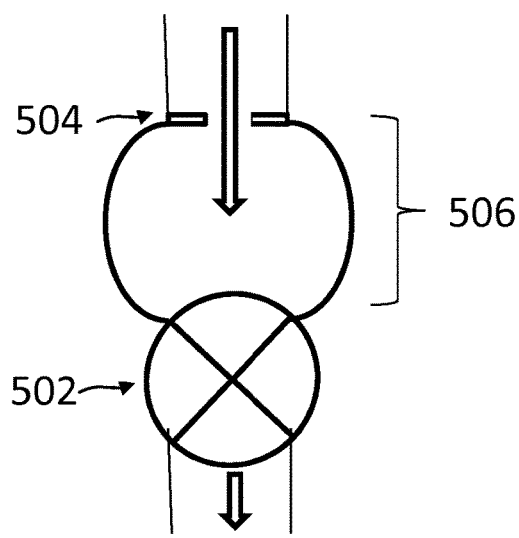
Figure 10H:
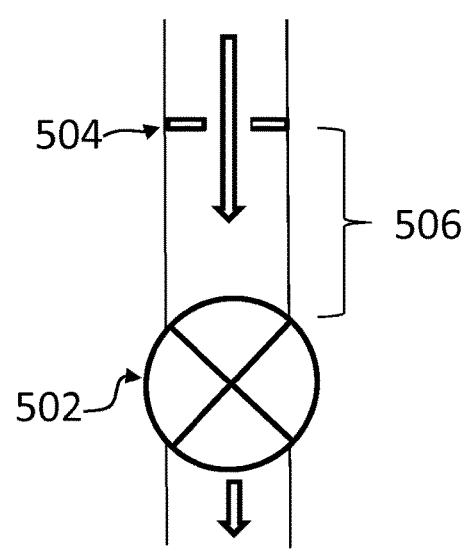

Referring to FIGS. 5A-9D, in exemplary embodiments, a desired flow profile that is substantially polygonal in shape can be generated and/or provided such that it includes an initial flow spike, as shown in FIGS. 5B, 6B, and 6D, and/or a waning flow, as shown in FIGS. 5D, 7B, 7D, 9B, and 9D, and/or a substantially rectangular shape, as shown in FIGS. 8B and 8D. The shape of the desired flow profile as well as attributes such as an initial flow spike and/or a waning flow can be generated and/or produced in response to, amongst other things, configuring a pharmaceutical gas delivery system such that the location of a first fixed flow valve 502 (e.g., flow valve 28, flow valve 30, etc.) can be upstream or downstream of a first fixed flow orifice 504 (e.g., a high flow orifice 32, low flow orifice 34, etc.) with a volumetric offset 506 located between and/or separating first fixed flow valve 502 and first fixed flow orifice 504 whereby first fixed flow valve 502 is rapidly opened and closed.

Referring to FIGS. 5A-5B, in exemplary embodiments, to generate and/or provide a desired flow profile 508 that includes an initial flow spike 510, a pharmaceutical gas delivery system can be configured to include a volumetric offset 506 located between and/or separating a first fixed flow orifice 504 located upstream to a first fixed flow valve 502, first fixed flow valve 502 being capable of rapidly actuating. In this configuration, desired flow profile 508 that includes initial flow spike 510 can be generated and/or provided to a patient by rapidly opening first fixed flow valve 502 at time (T1) to flow (Q1) causing an initial flow spike 510 of flow (Q2) of transient therapeutic gas to be generated and/or propagated to the patient. In exemplary embodiments, the volume of flow (Q2−Q1 for T2−T1) associated with initial flow spike 510 can be substantially equal to the volume in volumetric offset 506. In exemplary embodiments, this volume can be set to a desired amount to provide a specific initial flow spike to a patient.

Still referring to FIGS. 5A-5B, following desired flow profile 508, therapeutic gas flow can be provided to the patient for a duration of time (e.g., T2 to T3) until first fixed flow valve 502 is closed rapidly at T3 causing a sharp cutoff in flow of therapeutic gas to the patient.

Referring to FIGS. 5C-5D, in exemplary embodiments, to generate and/or provide a desired flow profile 512 that includes a waning flow 514, a pharmaceutical gas delivery system can be configured to include a volumetric offset 506 located between and/or separating a first fixed flow orifice 504 located downstream to a first fixed flow valve 502, first fixed flow valve 502 being capable of rapidly actuating. In this configuration, desired flow profile 512 can be generated and/or provided to a patient by rapidly opening first fixed flow valve 502 at time (T1) to flow (Q1) and continuing to flow therapeutic gas to a patient for a duration of time (e.g., T1 to T2).

Still referring to FIGS. 5C-5D, in exemplary embodiments, at time (T2) first fixed flow valve 502 can be closed rapidly ceasing flow through first fixed flow valve 502 while a volume of waning flow 514 can be provided to the patient until T3. In exemplary embodiments, the volume of flow associated with waning flow 514 can have a volume substantially equal to a volume in volumetric offset 506. In exemplary embodiments, this volume can be set to a desired amount to provide a specific waning flow to a patient.

Referring to FIGS. 6A-6D, in exemplary embodiments, the volume of flow (Q2−Q1 for T2−T1) associated with initial flow spike 510 of desired flow profile 508 can be adjusted by varying the amount of volumetric offset 506, and therefore volume, between and/or separating first fixed flow valve 502 and first fixed flow orifice 504. Referring to FIGS. 6A-6B, the volume of flow (Q2−Q1 for T2−T1) associated with initial flow spike 510 can be augmented by increasing the amount of volumetric offset 506, and therefore volume, between and/or separating first fixed flow valve 502 and first fixed flow orifice 504. Referring to FIGS. 6C-6D, the volume of flow (Q2−Q1 for T2−T1) associated with initial flow spike 510 can be reduced by decreasing the amount of volumetric offset 506, and therefore volume, between and/or separating first fixed flow valve 502 and first fixed flow orifice 504. Q2 may change as a result of varying the amount of volumetric offset 506 and/or Q2 may constant as the amount of volumetric offset 506 is varied with only the volume of flow (Q2−Q1 for T2−T1) associated with initial flow spike 510 changing.

Referring to FIGS. 7A-7D, in exemplary embodiments, the volume of flow associated with waning flow 514 of desired flow profile 514 can be adjusted by varying the amount of volumetric offset 506, and therefore volume, between and/or separating first fixed flow valve 502 and first fixed flow orifice 504. Referring to FIGS. 7A-7B, the volume of flow associated with waning flow 514 can be augmented by increasing the amount of volumetric offset 506, and therefore volume, between and/or separating first fixed flow valve 502 and first fixed flow orifice 504. Referring to FIGS. 7C-7D, the volume of flow associated with waning flow 514 can be reduced by decreasing the amount of volumetric offset 506, and therefore volume, between and/or separating first fixed flow valve 502 and first fixed flow orifice 504.

In exemplary embodiments, the shape and/or slope of waning flows and/or initial flow spikes can be modified and/or based on aspects of fixed flow rate assemblies and/or a pharmaceutical gas delivery system. In exemplary embodiments, waning flows and/or initial flow spikes can have linear and/or exponential shapes by modifying elements of fixed flow rate assemblies and/or a pharmaceutical gas delivery system such that flow is laminar and/or non-laminar. To produce laminar and/or non-laminar flow the ratio of the orifice's opening to tubing cross-section and/or volumetric offsets cross-section can be modified. To produce laminar and/or non-laminar flow the ratio of the shape of orifices and/or elements of fixed flow rate assemblies and/or a pharmaceutical gas delivery system can be modified.

As can be taken from FIGS. 6A-D and 7A-D, reducing the amount of volumetric offset 506 can adjust the flow profile to decrease the initial flow spike 510 and/or the waning flow 514. Accordingly, in exemplary embodiments, the amount of volumetric offset 506 can be minimized such that the initial flow spike 510 and/or the waning flow 514 is minimized, and thus producing a desired flow profile 508 or a desired flow profile 512 that is substantially rectangular in shape (e.g. a pulse wave).

Referring to FIGS. 8A-D, in exemplary embodiments, the volumetric offset 506 is negligible (and therefore not shown) such that the desired flow profile 508 or 512 is substantially rectangular in shape. As can be seen from FIGS. 8A-8B (first fixed flow orifice 504 located upstream from first fixed flow valve 502) and FIGS. 8C-8D (first fixed flow orifice 504 located downstream from first fixed flow valve 502), a pulse wave can be generated by having the first flow orifice 504 either upstream or downstream from the first fixed flow valve 502.

Accordingly, in exemplary embodiments, the amount of volumetric offset can be less than or equal to a certain volume, such as less than or equal to any of the following volumes: 5 mL, 4 mL, 3 mL, 2 mL, 1.5 mL, 1 mL, 0.9 mL, 0.8 mL, 0.7 mL, 0.6 mL, 0.5 mL, 0.4 mL, 0.3 mL, 0.2 mL, 0.15 mL, 0.1 mL, 0.09 mL, 0.08 mL, 0.07 mL, 0.06 mL, 0.05 mL, 0.04 mL, 0.03 mL, 0.02 mL, 0.015 mL, 0.01 mL, 0.009 mL, 0.008 mL, 0.007 mL, 0.006 mL, 0.005 mL, 0.004 mL, 0.003 mL, 0.002 mL, 0.0015 mL, 0.001 mL or 0.0005 mL.

In exemplary embodiments, smaller volumetric offsets can be used when the expected pulse of pharmaceutical gas is small, to ensure that any initial pulse spike and/or waning flow is only a small portion of the total pulse volume. For example, the volume of the pulse of pharmaceutical gas depends on the concentration of the pharmaceutical gas and the desired dose of pharmaceutical gas. Higher concentrations of pharmaceutical gas can result in smaller pulse volumes, and thus the volumetric offset can be smaller in pharmaceutical gas delivery systems that are designed to have small minimum pulse volumes or small average pulse volumes. Exemplary pulse volumes may be in the range of 0.1 mL to 30 mL, such as 30 mL, 25 mL, 20 mL, 15 mL, 10 mL, 9 mL, 8 mL, 7 mL, 6 mL, 5 mL, 4 mL, 3 mL, 2 mL, 1 mL, 0.9 mL, 0.8 mL, 0.7 mL, 0.6 mL, 0.5 mL, 0.4 mL, 0.3 mL, 0.2 mL or 0.1 mL.

In exemplary embodiments, the volumetric offset is only a certain proportion of a minimum pulse volume, average pulse volume, or maximum pulse volume that is expected for the pharmaceutical gas delivery system. In some embodiments, the volumetric offset has a volume that is less than or equal to a certain percentage of the minimum pulse volume, average pulse volume, or maximum pulse volume, such as less than or equal to any of the following percentages: 50%, 40%, 30%, 25%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.05% or 0.01%.

For some pharmaceutical gases and some diseases, it can be desired that the pulse of pharmaceutical gas is only delivered during a portion of the patient's inspiration, such as during the first ½ of inspiration, first ⅓ of inspiration, first ¼ of inspiration, etc. Accordingly, minimizing or eliminating the waning flow of a pulse volume can help ensure that the entire pulse of pharmaceutical gas is delivered during the desired window. In various embodiments, the entire pulse width (e.g. T1 to T3) is within a certain range, such as 10 milliseconds (msec) to 2 seconds (sec). Exemplary values within this range include 10 msec, 20 msec, 30 msec, 40 msec, 50 msec, 60 msec, 70 msec, 80 msec, 90 msec, 100 msec, 150 msec, 200 msec, 250 msec, 300 msec, 350 msec, 400 msec, 450 msec, 500 msec, 600 msec, 700 msec, 800 msec, 900 msec, 1 sec, 1.5 sec or 2 sec.

Referring to FIG. 9A-9D, in exemplary embodiments, a desired flow profile that is substantially triangular in shape can be provided and/or generated. In exemplary embodiments, with first fixed flow orifice 504 located downstream to first fixed flow valve 502 a substantially triangular desired flow profile can be generated and/or provided having (1) a sharp turn on of flow (Q1) provided to a patient by rapidly opening first fixed flow valve 502 at T1, (2) negligible flow can then be provided for a de minimis duration of time, and (3) after first fixed flow valve 502 closes rapidly at T2 flow through first fixed flow valve 502 can cease while the volume associated with waning flow 514 can continue to be provided to the patient until T3. Similar to above, the volume associated with waning flow 514 of a triangular desired flow profile can be adjusted by varying the amount of volumetric offset 506, and therefore volume, between and/or separating first fixed flow valve 502 and first fixed flow orifice 504.

Referring to FIGS. 10A-10H, in exemplary embodiments, the volume associated volumetric offset 506 can increased and/or decreased by adjusting the relative separation of first fixed flow orifice 504 to first fixed flow valve 502 and/or modifying the shape of volumetric offset 506. For example, referring to FIGS. 10D and 10H, the volume of volumetric offset 506 can increased and/or decreased by adjusting the relative separation of first fixed flow orifice 504 to first fixed flow valve 502. For another example, referring to FIGS. 10A-10C and 10E-10G the volume of volumetric offset 506 can increased and/or decreased by modifying the shape of volumetric offset 506 between first fixed flow orifice 504 to first fixed flow valve 502.

Figure 11A:
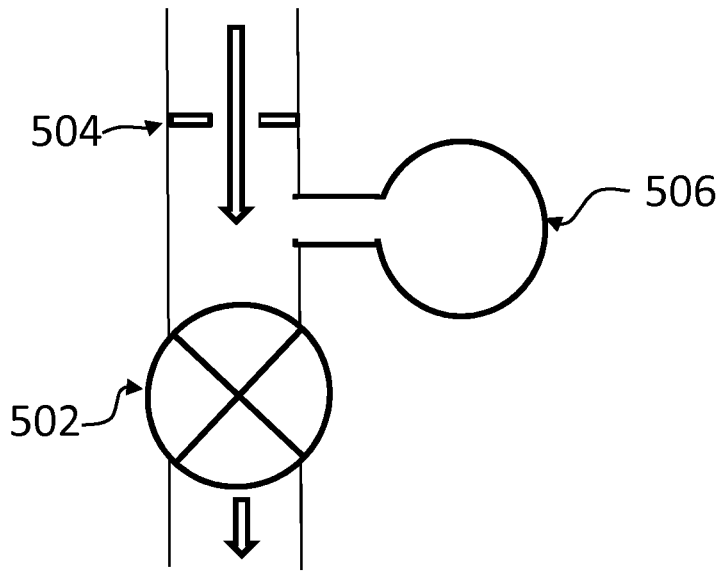
FIGS. 11A-11B illustratively depict additional exemplary volumetric offsets, in accordance with exemplary embodiments of the present disclosure.
Figure 11B:
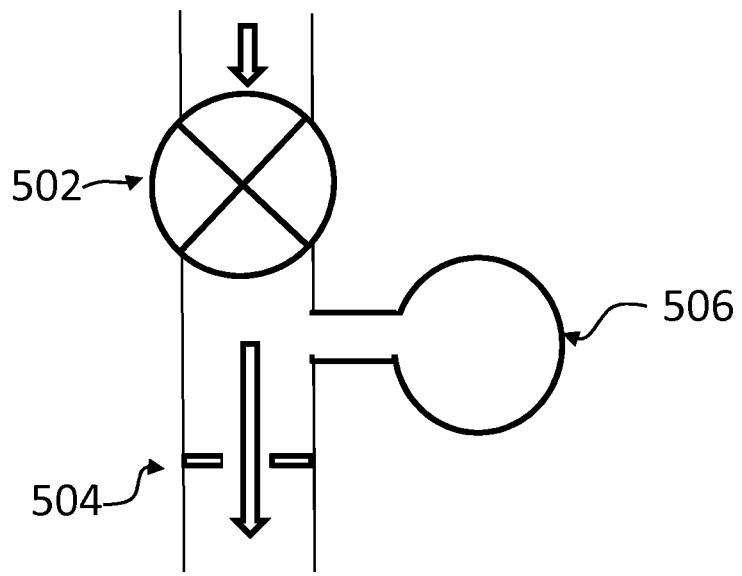

Referring to FIGS. 11A-11B, in exemplary embodiments, the volumetric offset can be a volume located off of a connection between and/or separating first fixed flow orifice to a first fixed flow valve. For example, volumetric offset 506 can be a separate reservoir providing volume between and/or separating first fixed flow orifice to a first fixed flow valve. For ease, at times, the volumetric offset is illustrated and/or described as being a volume between and/or separating a first fixed flow orifice to a first fixed flow valve. This is merely for ease and is in no way meant to be a limitation.

It will be understood that the volume associated with the volumetric offset can be increased and/or decreased by modifying the shape of the volumetric offset, the volumetric offset can be any shape, and/or the shape of the volumetric offset can be selected to modify the shape and/or properties of desired flow profiles generated and/or provided by a pharmaceutical gas delivery system. For ease, at times, the volumetric offset is illustrated and/or described as being increased and/or decreased by adjusting the relative separation of, and therefore volume, a first fixed flow orifice to a first fixed flow valve. This is merely for ease and is in no way meant to be a limitation.

In exemplary embodiments, systems and methods of the present disclosure can generate and/or provide desired flow profiles having varying flow rates using fixed flow valves. These desired flow profiles can provide flow rates beyond those of the on and off values of fixed flow valves used and/or associated with a pharmaceutical gas delivery system. By way of example, as described herein, pharmaceutical gas delivery systems using, for example, fixed flow assemblies can provide varying flow rates by taking into account spatial relationships of elements of the fixed flow rate assembly, rate of valve closure and opening, latent flows, transient wave generation and/or propagation, to name a few. This can allow for, amongst other things, more complex flow profiles without using expensive components (e.g., proportional flow valves)

Further, in exemplary embodiments, systems and methods of the present disclosure can generate and/or provide desired flow profiles having varying flow rates using multiple fixed flow valves. These desired flow profiles can provide flow profiles with flow rates beyond those of the on and off values, and/or cumulative on and off values, of the multiple fixed flow valves. At times, only one or two fixed flow valves are described. This is merely for ease and is in no way meant to be a limitation.

In exemplary embodiments, substantially complex desired flow profiles can be generated and/or provided that can have varying flow rates using fixed flow valves rather than proportional valves. Proportional valves can be substantially more expensive than fixed flow valves, and may not be as reliable and/or as predictable as fixed flow valves. Systems and methods of the present disclosure can allow for generating and/or providing substantially complex desired flow profiles without substantially increasing costs and/or without the use of substantially expensive proportional valves. Accordingly, using systems and methods of the present disclosure, a pharmaceutical gas delivery system can be fabricated and/or modified without including expensive components (e.g., proportional valves, etc.) and/or by reducing the number of expensive components used that can increase the cost of such systems, reduce availability to the public, and/or utilize resources that may be limited.

In exemplary embodiments, systems and methods of the present disclosure can generate and/or provide desired flow profiles having varying flow rates using one or more fixed flow valves as well as one or more proportional valve. Various desired flow profiles can be generated by the combination of one or more fixed flow valves with one or more proportional valve. At times, only fixed flow valves are described. This is merely for ease and is in no way meant to be a limitation.

Those skilled in the art will readily recognize numerous adaptations and modifications which can be made to the pharmaceutical gas delivery system and method of delivering a pharmaceutical gas of the present disclosure which will result in an improved method and system for introducing a known desired quantity of a pharmaceutical gas into a patient, yet all of which will fall within the scope and spirit of the present disclosure as defined in the following claims. Accordingly, the disclosure is to be limited only by the following claims and their equivalents.

Reference throughout this specification to "one embodiment," "certain embodiments," "one or more embodiments," "exemplary embodiment," "exemplary embodiments," and/or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment," "exemplary embodiment," "exemplary embodiments," and/or "in an embodiment" in various places throughout this specification are not necessarily referring to the same embodiment of the disclosure. Furthermore, the particular features, structures, materials, or characteristics can be combined in any suitable manner in one or more embodiments.

It will be understood that any of the steps described can be rearranged, separated, and/or combined without deviated from the scope of the disclosure. For ease, steps are, at times, presented sequentially. This is merely for ease and is in no way meant to be a limitation.

Further, it will be understood that any of the elements and/or embodiments of the disclosure described can be rearranged, separated, and/or combined without deviated from the scope of the disclosure. For ease, various elements are described, at times, separately. This is merely for ease and is in no way meant to be a limitation.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A system for providing a pulse of a pharmaceutical gas having a desired flow profile to deliver to a patient, the system comprising:
   a first fixed flow rate assembly including a first fixed flow valve in fluid communication with a first fixed flow orifice, the first fixed flow valve being (1) a fixed flow valve that rapidly opens and rapidly closes, (2) located upstream of the first fixed flow orifice and (3) at a volumetric offset from the first fixed flow orifice, wherein the volumetric offset has a volume of less than 0.1 mL; and
   a flow delivery control that rapidly opens and rapidly closes the first fixed flow valve located upstream of, and at the volumetric offset from, the first fixed flow orifice to provide a pulse of a pharmaceutical gas having a desired flow profile to a patient.

2. The system of claim 1, wherein the first fixed flow orifice downstream to the first fixed flow valve provides at least one of (1) a sharp turn on when the first fixed flow valve is opened rapidly, or (2) a waning flow having a volume substantially equal to a volume in the volumetric offset when the first fixed flow valve is closed rapidly.

3. The system of claim 1, wherein the volumetric offset is substantially minimized to decrease duration of a waning flow generated when the first fixed flow valve is closed rapidly.

4. The system of claim 1, wherein the volumetric offset has a volume of less than 0.05 mL.

5. The system of claim 1, wherein the volumetric offset has a volume in the range of 0.0005 mL to 0.05 mL.

6. The system of claim 1, wherein the desired flow profile for the pulse of pharmaceutical gas is one that minimizes the time that the first fixed flow valve is open.

7. The system of claim 6, wherein the first fixed flow valve provides a pulse having a pulse width of less than 500 milliseconds.

8. A method of providing a pulse of a pharmaceutical gas with a desired flow profile to deliver to a patient, the method comprising:
   rapidly opening a first fixed flow valve that is located upstream from a first fixed flow orifice to commence delivery of a first dose of a pharmaceutical gas in a pulse having a desired flow profile to a patient that abruptly increases flow to a desired initial flow rate over negligible time;
   rapidly closing the first fixed flow valve to end flow, through the first fixed flow valve, of the pharmaceutical gas; and
   providing a waning flow of the pharmaceutical gas after rapidly closing the first fixed flow valve to complete delivery, to the patient, of the pulse of the pharmaceutical gas with the desired flow profile, wherein the waning flow is generated in response to arranging the first fixed flow valve at a volumetric offset from the first fixed flow orifice, wherein the volumetric offset has a volume of less than 0.1 mL.

9. The method of claim 8, wherein the pulse of a pharmaceutical gas having a desired flow profile is provided to a patient to treat at least one of chronic obstructive pulmonary disease (COPD), idiopathic pulmonary fibrosis (IPF), and pulmonary hypertension (PH).

10. The method of claim 8, wherein the desired flow profile is downwardly sloped triangular shaped.

11. The method of claim 8, further comprising:
   maintaining open the first fixed flow valve to continue delivery, to the patient, of the pulse of the pharmaceutical gas with the desired flow profile at a desired continued flow rate for a period of time.

12. The method of claim 11, wherein the desired flow profile is quadrilateral shaped.

13. The method of claim 12, wherein the volumetric offset has a volume of less than 0.05 mL and the quadrilateral is substantially rectangular shaped.

14. The method of claim 8, wherein the pharmaceutical gas comprises nitric oxide.

15. The method of claim 14, wherein the concentration of nitric oxide in the pharmaceutical gas is 100 ppm to 5,000 ppm.

16. A method of providing a pulse of a pharmaceutical gas with a desired flow profile to deliver to a patient, the method comprising:
   rapidly opening a first fixed flow valve that is located downstream from a first fixed flow orifice to commence delivery of a first dose of a pharmaceutical gas in a pulse having a desired flow profile to a patient that abruptly increases flow to a desired initial flow rate including an initial flow spike over negligible time, wherein the initial flow spike is generated in response to arranging the first fixed flow valve at a volumetric offset from the first fixed flow orifice, wherein the volumetric offset has a volume of less than 0.1 mL; and rapidly closing the first fixed flow valve to end flow, through the first fixed flow valve, of the pharmaceutical gas to complete delivery, to the patient, of the pulse of the pharmaceutical gas with the desired flow profile.

17. The method of claim 16, wherein the pulse of a pharmaceutical gas having a desired flow profile is provided to a patient to treat at least one of chronic obstructive pulmonary disease (COPD), idiopathic pulmonary fibrosis (IPF), and pulmonary hypertension (PH).

18. The method of claim 16, further comprising:

maintaining open the first fixed flow valve to continue delivery, to the patient, of the pulse of the pharmaceutical gas with the desired flow profile at a desired continued flow rate for a period of time.

19. The method of claim 16, wherein the desired flow profile is substantially rectangular shaped.

* * * * *